United States Patent
Sheehan et al.

(10) Patent No.: US 7,985,192 B2
(45) Date of Patent: Jul. 26, 2011

(54) GEOMETRICALLY APERTURED PROTECTIVE AND/OR SPLINT DEVICE COMPRISING A RE-MOULDABLE THERMOPLASTIC MATERIAL

(75) Inventors: David Sheehan, County Waterford (IE); Morgan Tierney, County Offaly (IE)

(73) Assignee: Fastform Research Limited, County Waterford (IE)

( * ) Notice: Subject to any disclaimer, the term of this patent is extended or adjusted under 35 U.S.C. 154(b) by 950 days.

(21) Appl. No.: 11/662,191

(22) PCT Filed: Sep. 9, 2005

(86) PCT No.: PCT/IE2005/000098
§ 371 (c)(1),
(2), (4) Date: Mar. 8, 2007

(87) PCT Pub. No.: WO2006/027763
PCT Pub. Date: Mar. 16, 2006

(65) Prior Publication Data
US 2008/0154164 A1 Jun. 26, 2008

Related U.S. Application Data

(60) Provisional application No. 60/608,092, filed on Sep. 9, 2004.

(51) Int. Cl.
*A61F 5/00* (2006.01)
(52) U.S. Cl. .................................. 602/7; 602/5; 602/6
(58) Field of Classification Search .............. 602/5–8
See application file for complete search history.

(56) References Cited

U.S. PATENT DOCUMENTS

| | | | |
|---|---|---|---|
| 3,032,524 A | 5/1962 | Brewer | 260/29 |
| 3,375,822 A | 4/1968 | Rose | 128/90 |
| 3,728,206 A | 4/1973 | Buese | 161/112 |
| 3,906,943 A | 9/1975 | Arluck | 128/90 |
| 3,985,128 A | 10/1976 | Garwood et al. | 128/90 |

(Continued)

FOREIGN PATENT DOCUMENTS
CH 675963 11/1990
(Continued)

*Primary Examiner* — Kim M Lewis
(74) *Attorney, Agent, or Firm* — Jacobson Holman PLLC

(57) ABSTRACT

A protective and/or splint device, for example a distal radial splint device (200), comprises a protective and/or splint member (201) and a spacer member (13). The protective and/or splint member (201) comprises a composite protective and/or splint material and is formable at a forming temperature and is substantially rigid at ambient temperature. The material comprises a polycaprolactone and a ligno-cellulose additive material. The protective and/or splint member (201) comprises a mesh of elements (202), with a plurality of openings (203) through the protective and/or splint member (201). Away from the periphery of the splint member (201), the openings (203) are diamond-shaped. Two border elements (204) extend along the two sides of the periphery of the splint member (201). The three point bending strength to openness ratio of the member is greater than 0.1 and the unidirectional bending strength to openness ratio of the member is greater than 4. This results in a device (200) with sufficient strength, which is breathable with open surfaces, and the volume of material used is optimized. The strength of the member (201) parallel to the longitudinal direction of the arm is greater than the strength parallel too the circumferential direction. At the forming temperature the member (201) is stretchable. The member (201) is rounded between the outer surface of the member (201) and the edges around the openings (203).

36 Claims, 14 Drawing Sheets

U.S. PATENT DOCUMENTS

| | | | | |
|---|---|---|---|---|
| 4,013,798 A | 3/1977 | Goltsos | | 426/107 |
| 4,019,505 A | 4/1977 | Wartman | | 128/90 |
| 4,193,395 A | 3/1980 | Gruber | | 128/90 |
| 4,238,522 A | 12/1980 | Potts | | 427/2 |
| 4,240,415 A | 12/1980 | Wartman | | 128/90 |
| 4,273,115 A | 6/1981 | Holland et al. | | 128/90 |
| 4,286,586 A * | 9/1981 | Potts | | 602/7 |
| 4,385,024 A | 5/1983 | Tansill | | 264/223 |
| 4,401,113 A | 8/1983 | Incorvaia | | 128/156 |
| 4,411,262 A | 10/1983 | von Bonin et al. | | 128/90 |
| 4,433,680 A | 2/1984 | Yoon | | 128/90 |
| 4,473,671 A | 9/1984 | Green | | 523/105 |
| 4,502,479 A | 3/1985 | Garwood et al. | | 128/90 |
| 4,537,184 A | 8/1985 | Williams, Jr. | | 128/90 |
| 4,600,618 A | 7/1986 | Raychok, Jr. | | 428/92 |
| 4,609,578 A | 9/1986 | Reed | | 428/76 |
| 4,640,838 A | 2/1987 | Isakson et al. | | 426/107 |
| 4,661,535 A | 4/1987 | Borroff et al. | | 523/105 |
| 4,667,661 A | 5/1987 | Scholz et al. | | 128/90 |
| 4,768,502 A | 9/1988 | Lee | | 128/87 |
| 4,774,937 A | 10/1988 | Scholz et al. | | 128/90 |
| 4,888,225 A | 12/1989 | Sandvig et al. | | 428/71 |
| 4,946,726 A | 8/1990 | Sandvig et al. | | 428/76 |
| 5,318,504 A | 6/1994 | Edenbaum et al. | | 602/8 |
| 5,446,270 A | 8/1995 | Chamberlain | | 219/730 |
| 5,520,621 A | 5/1996 | Edenbaum et al. | | 602/8 |
| 5,584,800 A | 12/1996 | Scholz et al. | | 602/6 |
| 5,599,283 A | 2/1997 | Lindenmeyer | | 602/5 |
| 5,618,263 A | 4/1997 | Alivizatos | | 602/6 |
| 5,652,053 A | 7/1997 | Liegeois | | 442/150 |
| 5,662,596 A | 9/1997 | Young | | 602/26 |
| 5,733,647 A | 3/1998 | Moore, III et al. | | 428/304 |
| 5,752,926 A | 5/1998 | Larson et al. | | 602/7 |
| 5,807,291 A | 9/1998 | Larson et al. | | 602/8 |
| 5,830,167 A | 11/1998 | Jung | | 602/19 |
| 5,836,902 A | 11/1998 | Gray | | 602/5 |
| 5,980,474 A | 11/1999 | Darcey | | 602/5 |
| 6,074,354 A | 6/2000 | Scholz et al. | | 602/6 |
| 6,093,161 A | 7/2000 | Vlaeyen et al. | | 602/6 |
| 6,098,315 A | 8/2000 | Hoffmann, III | | 36/91 |
| 6,110,137 A | 8/2000 | Bastyr et al. | | 602/26 |
| 6,159,877 A | 12/2000 | Scholz et al. | | 442/103 |
| 6,241,567 B1 | 6/2001 | Evans | | 441/64 |
| 6,342,540 B1 | 1/2002 | Gluck et al. | | 521/56 |
| 6,547,468 B2 | 4/2003 | Gruenbacher | | 401/133 |
| 6,673,029 B1 | 1/2004 | Watson | | 602/6 |
| 6,695,801 B1 | 2/2004 | Toronto et al. | | 602/6 |
| 6,703,142 B2 | 3/2004 | Snow | | 428/522 |
| 2001/0031935 A1 | 10/2001 | Andersen | | 602/23 |
| 2001/0044247 A1 | 11/2001 | Evans | | 441/64 |
| 2002/0061690 A1 | 5/2002 | Evans | | 441/64 |
| 2002/0115784 A1 | 8/2002 | Datko et al. | | 524/824 |
| 2002/0143078 A1 | 10/2002 | Awokola et al. | | 522/81 |
| 2004/0077979 A1 | 4/2004 | Karason et al. | | 602/3 |
| 2004/0133137 A1 | 7/2004 | Hargis et al. | | 602/21 |
| 2004/0194352 A1 | 10/2004 | Campbell et al. | | 36/174 |
| 2007/0004993 A1 | 1/2007 | Coppens et al. | | 602/7 |

FOREIGN PATENT DOCUMENTS

| | | |
|---|---|---|
| EP | 472474 A1 * | 2/1992 |
| EP | 0770369 A1 | 5/1997 |
| FR | 2530946 | 2/1984 |
| GB | 2398269 A | 8/2004 |
| NL | 1001552 | 5/1997 |
| WO | WO97/33541 | 9/1997 |
| WO | WO99/20212 | 4/1999 |
| WO | WO2005/096759 | 10/2005 |
| WO | WO2006/077158 | 7/2006 |

* cited by examiner

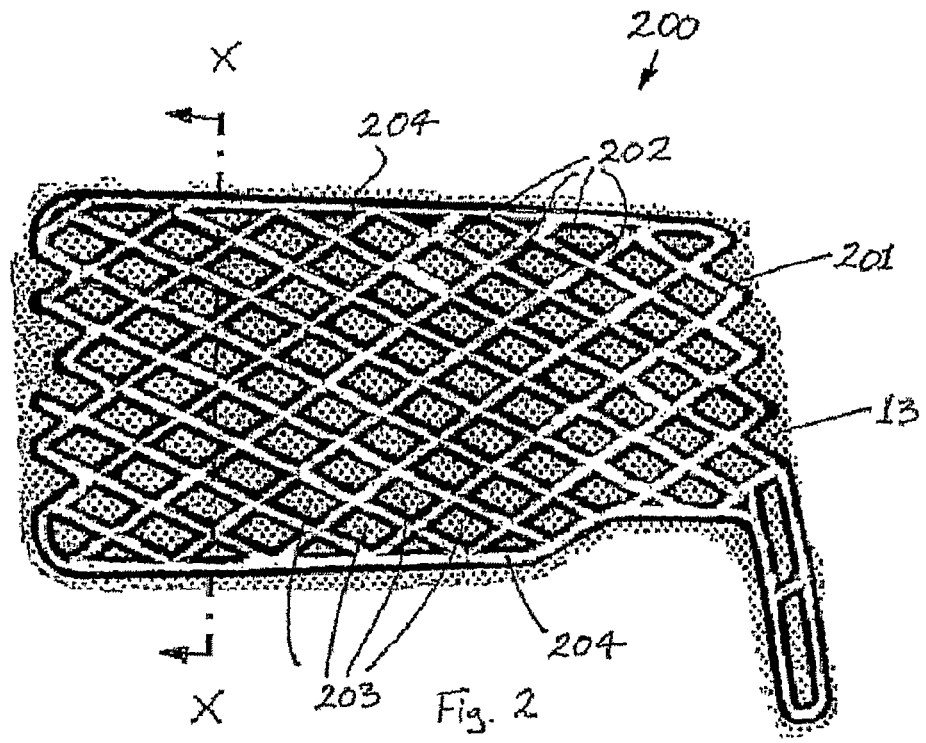
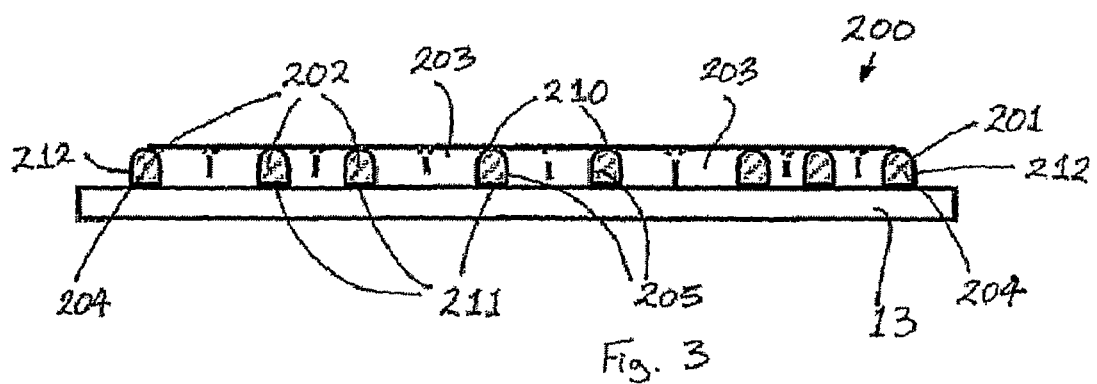

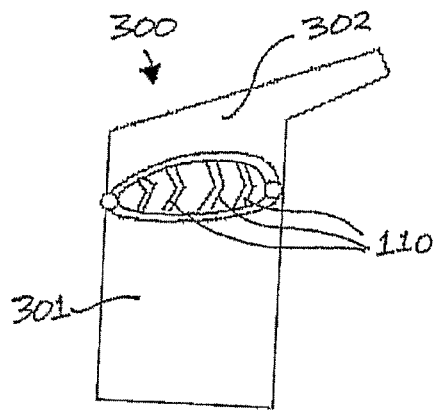
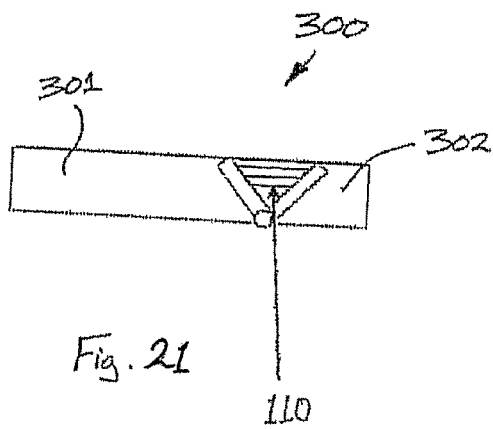
Fig. 20
Fig. 21
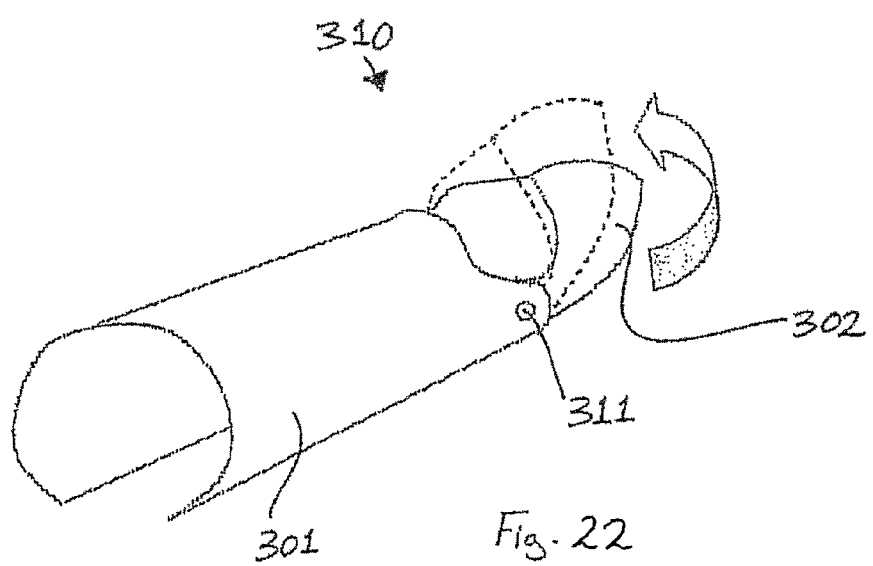
Fig. 22

US 7,985,192 B2

GEOMETRICALLY APERTURED PROTECTIVE AND/OR SPLINT DEVICE COMPRISING A RE-MOULDABLE THERMOPLASTIC MATERIAL

This is a national stage of PCT/IE05/000098 filed Sep. 9, 2005 and published in English, claiming benefit of U.S. provisional application No. 60/608,092, filed Sep. 9, 2004.

BACKGROUND OF THE INVENTION

This invention relates to a geometrically apertured protective splint device containing re-mouldable thermoplastic material that can be used as a composite splint material for immobilisation, bracing, casting, protection or support of limbs and body parts on humans and animals.

From here on in the term "device" will be used to denote the term geometrically apertured device containing re-mouldable thermoplastic material.

The term splint employed herein refers to an embodiment of the device in a sheet or a preformed sheet used for limb immobilisation, support and/or protection.

This invention relates to a splint device and to a composite material used for such.

Immobilisation of fractured or injured joints or limbs typically involves the process of restraining the joint or limb in place with a splint, cast, or brace. This is done to prevent the fractured/injured area from moving or being disturbed during the healing process.

Traditionally Plaster of Paris on fabric or gauze bandage has been used to form casts for the immobilisation of limbs. However Plaster of Paris has a number of disadvantages associated with it. For example Plaster of Paris is relatively heavy and bulky, has a slow setting time, cannot be reformed once set, possesses low impact resistance, and is susceptible to deterioration or damage once exposed to moisture thus making bathing and showering difficult. Additional concerns associated with the use of Plaster of Paris casting bandages are that they require a significant amount of time, usually 24 to 72 hours, to achieve their maximum strength, and that heat is generated from the exothermic setting reaction. Plaster of Paris also has poor radiopacity which prevents the continued monitoring of the limb during the healing process. In addition Plaster of Paris is substantially impervious to transmission of water vapour, such as perspiration. Thus Plaster of Paris traps moisture which can result in significant skin maceration.

One partial solution to improve breathability is the use of a thermoplastic mesh disclosed in U.S. Pat. No. 4,143,655, Custer et al. A negative drawback however with this method is the necessity to apply multiple layers of mesh to achieve adequate strength to support and protect body areas. Another drawback of this method is that the mesh needs to be trimmed in order to fit different body areas and this results in sharp edges that are formed due to trimming. Another disadvantage of this method is that underlying bandages, padding, dressings and gauzes can become wet because the material is usually heated using a hot water bath to soften the material to facilitate moulding. Moist dressings promote bacteria growth and can lead to discomfort and further complications.

It is usually prescribed that thermoplastic mesh and thermoplastic sheets with perforations are heated using a water bath. This will help to reduce the (unwanted) high tack characteristic associated with these materials which makes it otherwise difficult for the user to handle. However this means that these devices and materials are often wet when applied.

In the case of splints and casts it is important that devices and materials have sufficient strength to maintain correct alignment of fractured bones, or to restrict movement of a limb in order to promote healing, or to stabilise and help reduce swelling of injured limbs, or to protect a body area from impact and injury. In the case of fractured bones and where there is swelling or a risk of swelling it is an advantage if the devices or materials used have superior strength in the lateral direction along the limb to maintain firm alignment of the underlying fractured bone whilst it is a further advantage if the same devices or materials used have reduced strength and some slight flexibility around the circumferential direction of the limbs being covered in order that the device can be adjusted to compensate for swelling.

In cases where devices or materials are used to protect body parts from impact and injury it is important that the devices or materials have sufficient strength to withstand an impact and also be capable of transmitting/dissipating the force of the impact onto and across underlying padding or shock absorber materials to reduce or prevent injury to the underlying body part on humans and animals.

Those familiar in the art will recognise the importance of having breathable and open surfaces in devices and materials used for immobilisation, bracing, casting, protection or support of limbs and body parts on humans and animals in order to reduce skin maceration problems and clinical complications and to promote a reduction of healing times.

For wearer's comfort, minimisation of restrictions to natural body movements and to reduce recuperation times it is important that the weight of devices and materials used for immobilisation, bracing, casting and protection is kept to a minimum. Device design, volume of material used and material density are factors that influence the final weight of such devices.

We have discovered that three interdependent factors contribute significantly to the useful service performance of devices used for immobilisation, bracing, casting, protection or support of limbs and body parts on humans and animals.

These factors are:

The device has sufficient strength particularly in the lateral axis parallel to a limb The device has breathable and open surfaces to facilitate drying and aeration The volume of material used in the device is optimised for the intended device purpose We have combined a material with thermoplastic characteristics, and moulded profiled blanks containing geometric apertures to enable cost effective manufacture of devices that improve the useful service performance of devices used for immobilisation, bracing, casting, protection or support of limbs and body parts on humans and animals.

We herein disclose test techniques which produce numerical data showing the interdependent relationship of strength to surface openness as a function of the volume of material used, in optimised and non optimised devices.

Furthermore we disclose a most favourable Strength to Openness Index range whereby the relationship between the open surface area and strength of the revealed devices can be expressed in numerical format to show the superior properties of a geometrically apertured device consisting of a re-mouldable thermoplastic material also herein disclosed.

SUMMARY OF THE INVENTION

According to the invention there is provided a protective and/or splint device comprising a protective and/or splint member, the member comprising one or more openings therethrough, over at least part of the member, the three point bending strength to openness ratio ($S/O_3$) of the member being greater than 0.1, the $S/O_3$ being defined by:

$$S/O_3 = F/V \times \% OA$$

where
F=Force (N) required, during a three point bending test substantially as hereinbefore described, to deflect a sample of the member, having an area being tested of 100 cm², by 10 mm.
V=Volume (cm³) of the sample of the member $$\% OA = \left[ \frac{\text{The total area of the one or more openings}}{\text{The total area of the sample of the member}} \right] \text{Expressed as a percentage}$$

The $S/O_3$ may be in the range of from 0.1 to 5.0. The $S/O_3$ may be greater than 0.3. The $S/O_3$ may be in the range of from 0.3 to 4.0. The $S/O_3$ may be in the range of from 0.3 to 2.6. The $S/O_3$ may be in the range of from 0.3 to 0.45. The $S/O_3$ may be in the range of from 2.0 to 2.55.

In another aspect of the invention there is provided a protective and/or splint device comprising a protective and/or splint member, the member comprising one or more openings therethrough, over at least part of the member, the unidirectional bending strength to openness ratio ($S/O_u$) of the member being greater than 4, the $S/O_u$ being defined by:

$$S/O_u = F/V \times \% OA$$

where
F=Force (N) required, during a unidirectional bending test substantially as hereinbefore described, to deflect a sample of the member, having an area being tested of 100 cm², by 10 mm.
V=Volume (cm³) of the sample of the member $$\% OA = \left[ \frac{\text{The total area of the one or more openings}}{\text{The total area of the sample of the member}} \right] \text{Expressed as a percentage}$$

The $S/O_u$ may be in the range of from 4 to 20. The $S/O_u$ may be greater than 5. The $S/O_u$ may be in the range of from 5 to 15. The $S/O_u$ may be in the range of from 5 to 7. The $S/O_u$ may be in the range of from 8 to 9.5. The $S/O_u$ may be in the range of from 11 to 12.5.

In one embodiment the member defines a first direction and a second direction, over at least part of the member, the strength of the member in the first direction being greater than the strength of the member in the second direction. The flexural strength of the member in the first direction may be greater than the flexural strength of the member in the second direction. The first direction may be substantially orthogonal to the second direction. The first direction may be a longitudinal direction. The second direction may be a circumferential direction. The strength of the member in the second direction may be in the range of from 10% of 95% of the strength of the member in the first direction. The strength of the member in the second direction may be in the range of from 20% to 70% of the strength of the member in the first direction. The strength of the member in the second direction may be in the range of from 30% to 60% of the strength of the member in the first direction.

In one embodiment of the invention the member comprises one or more openings therethrough. The member may comprise a mesh of elements. The width of at least one of the elements may be in the range of from 2 mm to 12 mm. The width of at least one of the elements may be in the range of from 4 mm to 10 mm.

In one case the member comprises a border element along at least part of the periphery of the member.

The member may comprise three or more substantially straight edges around at least one of the openings. The member may comprise four substantially straight edges around at least one of the openings. A first acute angle may be subtended between two of the edges. A second acute angle may be subtended between two of the edges. A line passing through the apex of the first acute angle and through the apex of the second acute angle may be substantially parallel to the first direction. The acute angle may be in the range of from 15° to 85°. The acute angle may be in the range of from 30° to 80°. The acute angle may be approximately 60°. A first obtuse angle may be subtended between two of the edges. A second obtuse angle may be subtended between two of the edges. A line passing through the apex of the first obtuse angle and through the apex of the second obtuse angle may be substantially parallel to the second direction. The obtuse angle may be in the range of from 95° to 175°. The obtuse angle may be in the range of from 100° to 150°. The obtuse angle may be approximately 120°.

In one case at least one of the openings is substantially diamond-shaped.

In one case at least one of the openings is substantially parallelogram-shaped.

In one case the member comprises a substantially curved edge around at least one of the openings. At least one of the openings is substantially elliptical-shaped.

In one embodiment the length of the edge is in the range of from 2 mm to 30 mm. The length of the edge may be in the range of from 5 mm to 25 mm.

In another embodiment the member comprises a plurality of openings therethrough, and between each pair of adjacent openings the member comprises a junction. For at least one of the openings, the member may comprise a first junction on one side of the opening and a second junction on an opposite side of the opening. A line passing through the first junction and through the second junction may be substantially parallel to the first direction. For at least one of the openings, the member may comprise a third junction on one side of the opening and a fourth junction on an opposite side of the opening. A line passing through the third junction and through the fourth junction may be substantially parallel to the second direction. The distance between the first junction and the second junction may be greater than the distance between the third junction and the fourth junction. The distance between the third junction and the fourth junction may be in the range of from 10% to 95% of the distance between the first junction and the second junction.

In one embodiment over at least part of the member, the number of openings per decimetre is in the range of from 1 to 300. The number of openings per decimetre may be in the range of from 3 to 200. The number of openings per decimetre may be in the range of from 5 to 100. The number of openings per cm² may be constant over the splint member. The number of openings per cm² may vary over the splint member.

In another case over at least part of the member, the percentage of the total cross-sectional area of the one or more openings to the total cross-sectional area of the member is in the range of from 1% to 80%. The percentage of the total cross-sectional area of the one or more openings to the total cross-sectional area of the member is in the range of from 10% to 60%. The percentage of the total cross-sectional area of the one or more openings to the total cross-sectional area of the member may be in the range of from 15% to 50%.

In another case the device comprises a filler member configured to be located in the one or more openings.

In one embodiment at least part of the member is formable at a forming temperature above ambient temperature and is substantially rigid at ambient temperature. At ambient temperature, the strength of the member in the first direction may be greater than the strength of the member in the second direction. At the forming temperature the splint may be stretchable.

In another embodiment the member is substantially flat prior to forming. The member may be provided as a substantially flat component prior to forming.

In one case the member comprises an injection moulded member. In another case the member comprises a compression moulded member.

In a further embodiment the member comprises an outer surface for facing away from an object being protected and/or splinted, and one or more edges, over at least part of the member, the member being rounded between the outer surface and at least one of the edges.

The member may comprise a material as described below.

The invention also provides in another aspect a composite protective and/or splint material comprising a low melt polymer and a ligno-cellulose additive material.

In one embodiment the low melt polymer comprises a thermoplastic. The low melt polymer may comprise a copolymer. The low melt polymer may comprise a polycaprolactone. The additive material may comprise wood. The additive material may be provided in the form of a plurality of fibres. The fibres may be dispersed throughout the low melt polymer.

In one case the material is formable at a forming temperature above ambient temperature and is substantially rigid at ambient temperature. At ambient temperature, the Young's modulus of the material maybe in the range of from 300 MPa to 2,500 MPa. At ambient temperature, the Young's modulus of the material may be in the range of from 500 MPa to 2,000 MPa.

In one case the material forming temperature is above 35° C. The material forming temperature may be above 55° C.

In one case the material comprises a foaming agent.

In another case the material has enhanced heat insulation properties. The material may be configured to be moulded by hand and applied on a person's limb. The material may have reduced tack at the forming temperature. The ligno-cellulose additive material may at least partially assist in reducing tack at the forming temperature. The material may have improved melt strength. The ligno-cellulose additive material may at least partially assist in improving the melt strength. The material may be at least partially biodegradable.

In another aspect of the invention there is provided a protective and/or splint device comprising a protective and/or splint member comprising a material as described above.

In one case the member comprises a moulded member. The member may comprise an injection moulded member. The member may comprise a compression moulded member.

In another aspect the invention provides an injection moulded protective and/or splint member, at least part of the member being formable at a forming temperature above ambient temperature and being substantially rigid at ambient temperature.

The invention provides in a further aspect a compression moulded protective and/or splint member, at least part of the member being formable at a forming temperature above ambient temperature and being substantially rigid at ambient temperature.

In another aspect of the invention there is provided a splint material comprising a low melt polymer and a ligno-cellulose additive material.

The invention provides in a further aspect a protective and/or splint device comprising a protective and/or splint member, the member defining a first direction and a second direction, over at least part of the member, the strength of the member in the first direction being greater than the strength of the member in the second direction.

In one embodiment the flexural strength of the member in the first direction is greater than the flexural strength of the member in the second direction. The first direction may be substantially orthogonal to the second direction. The first direction may be a longitudinal direction. The second direction may be a circumferential direction. The strength of the member in the second direction may be in the range of from 10% to 95% of the strength of the member in the first direction. The strength of the member in the second direction may be in the range of from 20% to 70% of the strength of the member in the first direction. The strength of the member in the second direction is in the range of from 30% to 60% of the strength of the member in the first direction.

In one embodiment the member comprises one or more openings therethrough. The member may comprise a mesh of elements. The width of at least one of the elements may be in the range of from 2 mm to 12 mm. The width of at least one of the elements may be in the range of from 4 mm to 10 mm.

In one case the member comprises a border element along at least part of the periphery of the member.

In another embodiment the member comprises three or more substantially straight edges around at least one of the openings. The member may comprise four substantially straight edges around at least one of the openings. A first acute angle may be subtended between two of the edges.

A second acute angle may be subtended between two of the edges. A line passing through the apex of the first acute angle and through the apex of the second acute angle may be substantially parallel to the first direction. The acute angle may be in the range of from 15° to 85°. The acute angle may be in the range of from 30° to 80°. The acute angle may be approximately 60°. A first obtuse angle may be subtended between two of the edges. A second obtuse angle may be subtended between two of the edges. A line passing through the apex of the first obtuse angle and through the apex of the second obtuse angle may be substantially parallel to the second direction. The obtuse angle may be in the range of from 95° to 175°. The obtuse angle may be in the range of from 100° to 150°. The obtuse angle may be approximately 120°.

In one case at least one of the openings is substantially diamond-shaped.

In another case at least one of the openings is substantially parallelogram-shaped.

The length of the edge may be in the range of from 2 mm to 30 mm. The length of the edge may be in the range of from 5 mm to 25 mm.

In a further embodiment the member comprises a plurality of openings therethrough, and between each pair of adjacent openings the member comprises a junction. For at least one of the openings, the member may comprise a first junction on one side of the opening and a second junction on an opposite side of the opening. A line passing through the first junction and through the second junction is substantially parallel to the first direction. For at least one of the openings, the member may comprise a third junction on one side of the opening and a fourth junction on an opposite side of the opening. A line passing through the third junction and through the fourth junction may be substantially parallel to the second direction. The distance between the first junction and the second junction may be greater than the distance between the third junction and the fourth junction.

In another case over at least part of the member the number of openings per decimetre is in the range of from 1 to 300. The number of openings per decimetre may be in the range of from 3 to 200.

The number of openings per decimetre may be in the range of from 5 to 100. The number of openings per $cm^2$ may be constant over the splint member. The number of openings per $cm^2$ may vary over the splint member.

In another case over at least part of the member, the percentage of the total cross-sectional area of the one or more openings to the total cross-sectional area of the member is in the range of from 1% to 80%. The percentage of the total cross-sectional area of the one or more openings to the total cross-sectional area of the member may be in the range of from 10% to 60%. The percentage of the total cross-sectional area of the one or more openings to the total cross-sectional area of the member may be in the range of from 15% to 50%.

In one embodiment at least part of the member is formable at a forming temperature above ambient temperature and is substantially rigid at ambient temperature. At ambient temperature, the strength of the member in the first direction may be greater than the strength of the member in the second direction. At the forming temperature at least part of the member may be stretchable. The member may be substantially flat prior to forming. The member may be provided as a substantially flat component prior to forming.

In one case the member comprises an injection moulded member.

In another case the member comprises a compression moulded member. The member may comprise an outer surface for facing away from an object being protected and/or splinted, and one or more edges, over at least part of the member, the member being rounded between the outer surface and at least one of the edges.

The member comprises a material as described above.

In another aspect the invention provides a protective and/or splint device comprising a protective and/or splint member, the member comprising one or more substantially diamond-shaped openings therethrough.

In a further aspect the invention provides a protective and/or splint device comprising a protective and/or splint member, the member comprising one or more substantially parallelogram-shaped openings therethrough.

In another aspect of the invention there is provided a protective and/or splint device comprising a protective and/or splint member, the member comprising one or more substantially oval-shaped openings therethrough.

The invention also provides in another aspect a protective and/or splint device comprising a protective and/or splint member,
the member comprising a plurality of openings therethrough;
between each pair of adjacent openings the member comprising a junction; and
for at least one of the openings, the member comprising a first junction on one side of the opening, a second junction on an opposite side of the opening to the first junction, a third junction on another side of the opening and a fourth junction on an opposite side of the opening to the third junction;
the distance between the first junction and the second junction being greater than the distance between the third junction and the fourth junction.

In a further aspect the invention provides a protective and/or splint device comprising a protective and/or splint member, at least part of the member being formable at a forming temperature above ambient temperature and being substantially rigid at ambient temperature, at the forming temperature at least part of the member being stretchable.

In one embodiment the member defines a first direction and a second direction, and at the forming temperature the member is stretchable in the first direction and in the second direction. The first direction may be substantially orthogonal to the second direction. At the forming temperature the member may be stretchable in a longitudinal direction. At the forming temperature the member may be stretchable in a circumferential direction.

In one case the member comprises one or more openings therethrough. The member may comprise a mesh of elements. The width of at least one of the elements may be in the range of from 2 mm to 12 mm. The width of at least one of the elements may be in the range of from 4 mm to 8 mm.

In another case the member comprises a border element along at least part of the periphery of the member.

In a further case the member comprises three or more substantially straight edges around at least one of the openings. The member may comprise four substantially straight edges around at least one of the openings. A first acute angle may be subtended between two of the edges. A second acute angle may be subtended between two of the edges. The acute angle may be in the range of from 15° to 85°. The acute angle may be in the range of from 30° to 80°. The acute angle may be approximately 60°. A first obtuse angle may be subtended between two of the edges. A second obtuse angle may be subtended between two of the edges. The obtuse angle may be in the range of from 95° to 175°. The obtuse angle may be in the range of from 100° to 150°. The obtuse angle may be approximately 120°.

In one case at least one of the openings is substantially diamond-shaped.

In another case at least one of the openings is substantially parallelogram-shaped.

The length of the edge may be in the range of from 2 mm to 30 mm. The length of the edge may be in the range of from 5 mm to 25 mm.

At least one of the openings may be oval-shaped.

In another case the member comprises a plurality of openings therethrough, and between each pair of adjacent openings the member comprises a junction. For at least one of the openings, the member may comprise a first junction on one side of the opening and a second junction on an opposite side of the opening. For at least one of the openings, the member may comprise a third junction on one side of the opening and a fourth junction on an opposite side of the opening. The distance between the first junction and the second junction may be greater than the distance between the third junction and the fourth junction.

In one embodiment over at least part of the member the number of openings per decimetre is in the range of from 1 to 300. The number of openings per decimetre may be in the range of from 3 to 200. The number of openings per decimetre may be in the range of from 5 to 100. The number of openings per $cm^2$ may be constant over the splint member. The number of openings per $cm^2$ may vary over the splint member.

In one case over at least part of the member the percentage of the total cross-sectional area of the one or more openings to the total cross-sectional area of the splint member is in the range of from 1% to 80%. The percentage of the total cross-sectional area of the one or more openings to the total cross-sectional area of the splint member may be in the range of from 10% to 60%. The percentage of the total cross-sectional area of the one or more openings to the total cross-sectional area of the member may be in the range of from 15% to 50%.

In another case the member comprises an injection moulded member.

In a further case the member comprises a compression moulded member.

The member may comprise an outer surface for facing away from an object being protected and/or splinted, and one or more edges, over at least part of the member, the member being rounded between the outer surface and at least one of the edges.

The member may comprise a material as described above.

The member may be substantially flat prior to forming. The member may be provided as a substantially flat component prior to forming.

In another aspect of the invention there is provided a protective and/or splint device comprising a protective and/or splint member;
 at least part of the member being formable at a forming temperature above ambient temperature and being substantially rigid at ambient temperature;
 the member comprising an outer surface for facing away from an object being splinted and/or protected, and one or more edges;
 over at least part of the member the member being rounded between the outer surface and at least one of the edges.

In one embodiment the member comprises a plurality of edges, and the member is rounded between the outer surface and each of the edges. The member may comprise one or more openings therethrough. The member may comprise a mesh of splint elements.

The member may comprise one or more edges around at least one of the openings. The member may comprise one or more edges around a periphery of the member.

In one case the member comprises an inner surface for facing towards an object being splinted and/or protected. The member may comprise a corner between the inner surface and the edge. The angle subtended between the inner surface and the edge may be approximately 90°.

In one case the member comprises an injection moulded member.

In another case the member comprises a compression moulded member.

The cross-sectional profile of the member may be constant over the member.

The cross-sectional profile of the member may vary over the member.

In one case at the forming temperature at least part of the member is stretchable.

The member may comprise a material as described above.

The member may be substantially flat prior to forming. The member may be provided as a substantially flat component prior to forming.

In another case over at least part of the member the thickness of the member is in the range of from 0.2 mm to 10 mm. The thickness of the member may be in the range of from 2 mm to 8 mm. The thickness of the member may be in the range of from 3 mm to 7 mm. The thickness of the member may be constant over the splint member. The thickness of the member may vary over the splint member.

In one case the member comprises a polymeric material.

In another case the device comprises a spacer member configured to be located between the member and an object being splinted and/or protected. The spacer member may be attached to the member. The spacer member may comprise a foam. The spacer member may comprise a padding bandage.

In another case the device comprises a cover member for covering the member. The cover member may be configured to facilitate selective uncovering of the member. The cover member may be configured to enclose the member. The cover member may be selectively openable.

In one case the member comprises a first layer and a second layer, at the forming temperature the first layer being movable relative to the second layer. The first layer may be hingable relative to the second layer.

In one case the member comprises a mesh, the mesh comprising a single uniform flat material with diamond-shaped openings therethrough, the mesh being movable relative to adjoining diamond openings due to a concertina effect and due to stretching of the composite material of the member when the member is at the forming temperature.

The combined effect of movement may result in extensibility of up to plus 40% or minus 20% of the member.

In another case the device comprises a first member and a second member, at ambient temperature the first member being movable relative to the second member. At ambient temperature the first member may be hingable relative to the second member.

The member may comprise one or more openings. At least one of the openings may be preformed. The member may be a moulded member. The member may be non-perforated.

In one embodiment the member is configured to extend around only a part of an object being splinted and/or protected.

The device may comprise a mid-humerus brace.

The device may comprise a distal radial splint.

The device may comprise a body protection device.

The device may comprise a therapeutic or occupational protection device.

In a further embodiment the invention provides a method comprising the steps of:—
 providing a protective and/or splint member, the member being formable at a forming temperature above ambient temperature and being substantially rigid at ambient temperature;
 heating the member to the forming temperature;
 forming the member around an object; and
 facilitating cooling of the member to ambient temperature around the object.

In one embodiment the member is activated by heating, such as by hot water, convection, irradiation.

The member may be at least partially stretched during forming of the splint member around the object. The member may comprise a stretchable mesh. The member may be stretched by hinging the first layer relative to the second layer.

In one case the member comprises a mesh, the mesh comprising a single uniform flat material with diamond-shaped openings therethrough, the mesh being moved relative to adjoining diamond openings due to a concertina effect and due to stretching of the composite material of the member when the member is at the forming temperature.

The combined effect of movement may result in extensibility of up to plus 40% or minus 20% in the member.

In another case the method comprises the step of, at ambient temperature, moving a first member relative to a second member.

The member comprises a material as described above.

In one case the method comprises the step of removing the member from the object. At least part of the member may be cut to remove the member from the object. The member may comprise a mesh of elements. One or more of the elements may be cut.

The invention provides in one embodiment a method of splinting and/or protecting as described above.

The invention provides in another aspect a cutting device for cutting at least part of a protective and/or splint device to remove the device from an object being splinted and/or protected.

In one case the cutting device is configured to remove a device comprising a mesh of elements from an object being splinted and/or protected. The cutting device may be configured to cut one or more elements. The cutting device may comprise a first cutting blade movable relative to a second cutting blade to cut at least part of a device. The cutting device may be configured to minimise cutting/pinching of a surface of the object being splinted and/or protected.

The invention provides a thermoplastic mouldable device which has several advantages. The device comprises a foraminous plaque which is manufactured and supplied in a flat format to minimise storage and transportation costs. On requirement, the device is heated above the forming temperature of the material which can then be draped, moulded and cooled forming a rigid highly breathable splint device. As the device can be provided pre-sized, minimum time or skill is required to apply such a splint device. The device may be applied as a single unit. It is not necessary to prepare the device by adding section after section.

The flat heat mouldable device disclosed herein has a 'strength to openness index' of 5.0 or greater when measured using the unidirectional test technique and a strength to openness index along one axis of 0.3 or greater when measured using the three point bending test apparatus. The apertures should be of the range of 1 to 300 apertures/decimetre, preferably 3 to 200 apertures/decimetre and most preferably 5 to 100 apertures/decimetre.

The flexural strength of the splint member in the circumferential direction to the limb axis to which it is applied may be in the range of from 10% to 95% of the flexural strength of the splint member in the direction parallel to the limb axis, and is preferably in the range of from 20% to 80% of the flexural strength.

Applying the principles of the invention allows splint devices to be produced which match the geometry of the limb to which they are applied. This is especially valuable when the technology is used in sized splint forms. This ensures that the moulded splint device neatly conforms to the wearer's limb.

On activation the device may be stretched up to 40% without a significant change in the rib thickness, due to the concertina design disclosed here in.

The outer surface of the elements facing away from an object being splinted can be rounded to reduce the likelihood of snagging.

The additive material enhances the mechanical properties of the polycaprolactone. The fibre filler, for example a lignocellulose material, can increase the flexural rigidity of the matrix polymer by up to a factor of 3 without impeding its biodegradability. The material forming temperature is above 35° C., preferably above 50° C., and in this case is above 57° C. At ambient temperature, the Young's modulus of the composite material is in the range of from 400 MPa to 2,500 MPa, and is preferably in the range of from 500 MPa to 2,200 MPa.

As both polycaprolactone and wood are biodegradable materials, by using wood as the additive material this ensures that the composite splint material is an environmentally-friendly material. Wood fibres, such as sawdust, which may be used as the additive material, are an economical and widely-available resource. Under incineration polycaprolactone produces $CO_2$ and $H_2O$. In addition lignocellulose materials are cost effective, natural and renewable additives.

In particular when the composite splint material is at the forming temperature, the additive material provides a degree of bulk to the polycaprolactone which results in a more easy to handle material with reduced tackiness. It is thus easier to arrange the flexible composite material in a desired location and/or orientation around an object without the composite material becoming flattened down.

By dispersing the fibres throughout the polycaprolactone, this assists in creating a homogenous composite splint material with uniform properties which can be produced on conventional thermoplastic processing equipment.

It should also be noted that the lignocellulose additive material has been found to reduce the likelihood of heat discomfort during or after activation when handling. This improvement may be attributed to the improved insulation properties of the composite splint material and to the plurality of wood fibre points at the interface surface of the material. This reduces the rate of thermal energy flow to adjacent surfaces. This is particularly useful when moulding by hand as the material is easy to handle and does not feel hot.

Foaming of the composite splint material is also possible by the addition of foaming agents in the composite material, for example water, Doping of the foaming agents with suitable microwave irradiation absorbers, such as susceptors, ensures that the foaming agents heat rapidly when exposed to microwave irradiation and thereby expand inside the softened composite material to produce a cellular structure throughout.

The composite splint material of the invention can also be used with conventional polymeric additives such as filler, pigments, plasticizers, blowing agents, flame retardants, stabilisers, and fragrances.

This openness may be especially advantageous in the case where the splint device is employed to splint a part of a patient's body for long periods of time. Therefore the risk of skin maceration, irritation and the conditions conducive to bacteria growth are reduced. The openings also allow the device and liner to dry quickly. In the case of splints, showering and bathing is possible. Also the device may be washed for hygiene.

The large openings also have advantages where access to the underlying limb is required without the necessity of creating windows in the device. Application examples include; indwelling devices, light treatments, probes, imaging, pharmaceuticals, gasses, injections, topical sprays, ultrasonic devices, electrical devices and circuitry, neuromuscular stimulation devices and percutaneous pinning. An important requirement for a splint device is to support and maintain bone alignment around the fracture site. The splint device of the invention achieves support without having any substantial product weight increase. According to the invention a splint device has been devised where both the resistance to bending and the openness of the splint device have been optimised. The high level of openness allows the splint device to be thicker with a minimum increase in splint weight/volume per unit area.

The disclosed devices allow for strength variations, i.e. anisotropic characteristics in the splint device, by selecting the geometries of the openings. Therefore the performance of the splint device may be controlled to meet the user requirements. This characteristic can be of significant value achieving maximum limb support on the longitudinal direction yet allows for reduced rigidity in the circumferential limb axis. This allows for swelling while limb alignment is retained.

In one preferred embodiment the splint device is supplied with a rounded outer surface to reduce snagging on the wearer's clothes. There is also a risk of snagging on objects such as table corners where large openings exist. We have found that the rounded channels greatly reduce the risk for such. In addition the design of the splint member allows for a significant reduction in cross sectional area and therefore product weight without sacrificing on limb contact support by tapering/rounding the channels away from the limb. The use of tapered or rounded outer surfaces also aids manufacturing by easing mould release.

The openings ensure that the splint member is breathable. This may be especially advantageous in the case where the splint device is employed to splint a part of a patient's body. Therefore the risk of skin maceration, irritation and the conditions conducive to bacteria growth are reduced. These openings also allow the splint device to dry quickly. In the case of the splint device, showering and swimming is possible, unlike with Plaster of Paris. The splint device of the invention can be washed.

The mesh shape, for example a diamond mesh shape, enables the splint member to be easily arranged around an object in a desired location and/or orientation, and to be stretched for sizing if necessary.

In the case of the splint device, to improve compliance and to facilitate extensibility of the device during forming, the diamond mesh may be aligned parallel with the centre line of the limb being treated. This design characteristic also allows the splint device to be used as a full cast. The splint device can also be 'over coated' with synthetic resin materials where extra reinforcement is necessary.

The diamond mesh also provides excellent shock distribution during impact.

The mesh design allows up to 40% stretch and good compliance.

Advantages of the diamond-shaped openings in the splint member include:

The diamond mesh is conformable, pliable, stretchable and compressible.

The application process is easy and fast to apply, and is a dry process.

The mesh configuration of the splint member provides good shock distribution.

The mesh configuration of the splint member provides good support and protection such as for sports injuries and/or protection from further injuries.

The mesh configuration of the splint member reduces the risk of itch and allows the wearer to scratch underlying itchy areas.

Trimming of the splint device when activated can result in a rounded edge. This is a result of the lignocellulose additive material drawing down the material edge during cutting. The material does not produce dust during trimming or cutting unlike conventional moulding materials, such as Plaster of Paris, and synthetic cast materials.

When the splint device is being used to splint a part of a patient's body, a padding bandage, foam or spacer member acts to provide a barrier between the splint member and the skin of the patient. Thus the heat or rigidity of the splint member is prevented from causing discomfort to the patient. In addition, the splint member protects the patient's skin in the case where the splint member is tacky.

By enabling the splint members to move relative to one another, this ensures that the splint device may be adjusted or removed from an object even when the splint members are substantially rigid.

By designing the splint device with a series of elements, this ensures that the splint device may be adjusted or removed from the object being splinted even when the splint members are rigid, for example using a hinge system. The hinge system may also be incorporated as part of a laminate system with padding, foaming, or spacer fabrics. In one example the support fabric may act as the hinge for the system. This ensures a complete system, making its application simple and efficient for example in the case of a splint device.

The composite splint material of the invention may be compounded on conventional equipment, such as two roll mill and extrusion. Likewise moulding may be carried out using compression, transfer or injection moulding and related techniques.

In one embodiment the present invention relates to a radiation activated moulding article comprising a novel thermoplastic composite, and a technique for producing the same. The invention may be activated via conventional heating or microwave radiation. The invention may be used for example in an orthopaedic splint or cast. On activation the thermoplastic composite becomes soft and drape-like allowing the user to work the article into the required shape. On cooling the article forms a rigid splint preserving its shape throughout its lifetime.

Application areas of the invention include braces, splinting fixation and casting bandaging for orthopaedic applications, custom moulded seating, handles and grips, degradable cutlery, protective padding such a shin guards for humans or animals, foot orthotics, braces and support for ulcerated foot conditions, hip protectors.

According to the invention there is provided a composite material suitable for use in moulding;

the material having a flexible configuration at a forming temperature above ambient temperature, and a rigid configuration at ambient temperature; and the material comprising:— a low melt polymer; and an additive material.

In one case the low melt polymer comprises a thermoplastic. In another case the low melt polymer comprises a co-polymer. In a further case the low melt polymer comprises a polycaprolactone.

The additive material enhances the mechanical properties of the polycaprolactone. In particular when the composite material is in the flexible configuration at the forming temperature, the additive material provides a degree of bulk to the polycaprolactone which results in a more easy to handle composite material with reduced tackiness. It is thus easier to arrange the flexible composite material in a desired location and/or orientation around an object without the composite material becoming flattened down.

In addition the additive material may expand upon heating, if required, resulting in a larger cross-sectional area. In this manner the strength to weight ratio of the composite material in the flexible configuration and in the rigid configuration is improved.

Preferably the material forming temperature is above 40° C. Ideally the material forming temperature is above 50° C. Most preferably the material forming temperature is above 57° C.

In one embodiment of the invention the additive material is provided in the form of a plurality of fibres. Preferably the fibres are dispersed throughout the polycaprolactone.

By dispersing the fibres throughout the polycaprolactone, this assists in creating a homogenous composite material, with uniform properties.

The additive material may comprise a water-retaining material. Preferably the additive material comprises water.

When the water is present in the additive material, the water may act as a susceptor. This aspect is especially advantageous in the case when the composite material is heated using microwave heating. The susceptor absorbs the microwave irradiation resulting in a faster and more efficient heating of the composite material. In addition the use of water greatly improves the heat distribution within the relatively insulating composite and reduces the likelihood of hot and cold spots during activation. This characteristic can be further utilised by creating an efficient environment within the device packaging. When irradiated within a bag, the steam generated greatly improves heating efficiency and distribution of the device.

In one case the additive material comprises a ligno-cellulosic material. Preferably the additive material comprises wood.

As both polycaprolactone and wood are biodegradable materials, by using wood as the additive material this ensures that the composite material is an environmentally-friendly material.

Wood fibres, such as sawdust, which may be used as the additive material, are an economical and widely-available resource.

The additive material may comprise carbon. The additive material may comprise mica. The additive material may comprise polyanaline.

In one case the material comprises a foaming agent.

The material may comprise an irradiation absorber.

In another aspect of the invention there is provided a device comprising:—
 a mouldable member comprising a material of the invention.

In one embodiment the device comprises a spacer member configured to be located between the mouldable member and an object.

When the device is being used to splint a part of a patient's body, a bandage foam or spacer member acts to provide a barrier between the mouldable member and the skin of the patient. Thus the heat or rigidity of the mouldable member is prevented from causing discomfort to the patient. In addition, the mouldable member protects the patient's skin in the case where the mouldable member is tacky.

Trimming of the device when activated results in a rounded edge. This is a result of the lignocellulose component drawing down the material edge during cutting. This material does not produce dust during trimming or cutting unlike many conventional moulding materials such as Plaster of Paris.

It should also be noted that the lignocellulose compound has been found to reduce the likelihood of heat discomfort during or after activation when handling. This improvement may be attributed to the improved insulation properties of the composite and the plurality of wood fibre points at the interface surface of the material. This reduces the rate of thermal energy flow to adjacent surfaces. This is particularly useful when moulding by hand as the material is easy to handle and does not feel hot. This is particularly useful were the material is moulded by children.

The mouldable member may comprise one or more openings. Preferably the device comprises a filler member configured to be located in the one or more openings.

The openings ensure that the mouldable member is breathable. This may be especially advantageous in the case where the device is employed to splint a part of a patient's body. Therefore the risk of skin maceration, irritation and the condition conducive to bacteria growth are reduced. These openings also allow the device to dry quickly, in the case of splints and casts showering (The cast can be washed) and swimming is possible unlike Plaster of Paris.

Another advantage of this system in relation to splints and casts is in its ability to be remoulded locally or entirely. This has benefits over conventional cast materials, and can be very valuable where the wearer suffers from swelling. Local remoulding can be carried out with a hot airgun or a hair dryer.

Ideally the mouldable member is provided at least partially in the form of a mesh. Most preferably the mesh defines substantially diamond-shaped openings therethrough.

The mesh shape, in particular the diamond mesh shape, enables the mouldable member to be easily arranged around an object in a desired location and/or orientation, and to be stretched if necessary.

In the case of a splint or cast, to improve compliance and to facilitate extensibility of the device during moulding the diamond mesh is aligned parallel with the centre line of the limb being treated. This design characteristic also allows the system to be used as a full cast, without seam lines. The system can also be 'over coated' with synthetic resin materials where extra reinforcement is necessary.

The diamond mesh system also provides excellent shock distribution during impact.

The mesh may comprise a first layer and a second layer, and the first layer is movable relative to the second layer when the mouldable member is in the flexible configuration. Preferably the first layer is hingable relative to the second layer.

The mesh may comprise a single uniform flat material with diamond-shaped openings therethrough, the mesh being movable relative to adjoining diamond openings due to the concertina effect and due to stretching of the composite material within the mouldable member when the mouldable member is in the flexible configuration. Preferably the combined effect of movement results in extensibility of up to (plus or minus) 30% in the mouldable member made from the composite material and configured with diamond openings/mesh.

In another embodiment the device comprises a cover member suitable for covering the mouldable member. Preferably the cover member is configured to facilitate selective uncovering of the mouldable member. The cover member may be configured to enclose the mouldable member. Preferably the cover member is selectively openable.

In another case the device comprises an indicator to indicate when the mouldable member is at the forming temperature. Preferably the indicator comprises a visual indicator. Ideally a part of the device is configured to become transparent at the forming temperature. The indicator may comprise a marking visible only when the part of the device is transparent.

The heating of the mouldable member may be performed in a highly efficient manner by using the indicator to indicate to the user when the mouldable member is at the forming temperature.

In a further embodiment the device comprises a first mouldable member and a second mouldable member, the first mouldable member in the rigid configuration being movable relative to the second mouldable member in the rigid configuration. Preferably the first mouldable member in the rigid configuration is hingable relative to the second mouldable member in the rigid configuration.

By enabling the mouldable members to move relative to one another, this ensures that the device may be adjusted or removed from an object even when the mouldable members are in the rigid configuration.

By designing the device with a series of elements, this ensures that the device may be adjusted or removed from the object being moulded even when the members are in the rigid configuration, i.e. a hinge system. The system can also be incorporated as part of a laminate system with padding, foaming, or spacer fabrics. This ensures a complete system, making its application simple and efficient, especially in the case of cast and back-slabs.

The invention also provides in a further aspect a device comprising:—
- a mouldable member comprising polycaprolactone;
- the mouldable member having a flexible configuration at a forming temperature above ambient temperature, and a rigid configuration at ambient temperature;
- the mouldable member being provided at least partially in the form of a mesh.

In one case the invention provides a splint device.

In another aspect of the invention there is provided a method comprising the steps of:—
- providing a mouldable member having a flexible configuration at a forming temperature above ambient temperature, and a rigid configuration at ambient temperature;
- heating the mouldable member to the forming temperature;
- arranging the mouldable member in the flexible configuration around an object; and
- facilitating cooling of the mouldable member to ambient temperature around the object.

In one case the mouldable member is heated by microwave heating.

The mouldable member may be at least partially stretchable during arranging of the mouldable member around the object. Preferably the mouldable member is provided at least partially in the form of a mesh, and the mouldable member is stretched by moving a first layer of the mesh relative to a second layer of the mesh. Ideally the mouldable member is stretched by hinging the first layer relative to the second layer. The mouldable member may comprise a mesh having a single uniform flat material with diamond-shaped openings therethrough, the mesh being movable relative to adjoining diamond openings due to the concertina effect and due to stretching of the composite material within the mouldable member when the mouldable member is in the flexible configuration. Preferably the combined effect of movement results in extensibility of up to (plus or minus) 30% in the mouldable member made from the composite material and configured with diamond openings/mesh.

In one embodiment the method comprises the step of monitoring an indicator to determine when the mouldable member is at the forming temperature. Preferably the indicator is monitored by visually observing the indicator.

In one case the method comprises the step of moving a first mouldable member in the rigid configuration relative to a second mouldable member in the rigid configuration.

In another embodiment the mouldable member comprises a material of the invention.

The invention provides in one case a method of splinting.

In a further aspect the invention provides a medical device comprising a mouldable member, the mouldable member comprising one or more openings.

In one embodiment the mouldable member has a flexible configuration at a forming temperature above ambient temperature, and a rigid configuration at ambient temperature.

Preferably the mouldable member is provided at least partially in the form of a mesh. Ideally the mesh defines substantially diamond-shaped openings therethrough.

In one case the invention provides a splint device.

Preferably the mesh configuration provides good shock distribution. Ideally the mesh configuration provides good support and protection such as for sports injuries and/or protection from further injuries. Most preferably the mesh configuration reduces risk of itch and allows wearer to scratch underlying itchy areas.

The Mesh design allows up to 30% stretch and good compliance. This also ensures that device can be used as a full cast without seams.

The material is radio-transparent and therefore as a cast system does not need to be removed for X-ray.

It should be noted that the systems revealed above can also be used with conventional polymeric additives such as filler, pigments, plasticizers, blowing agents, flame retardants, stabilisers, and fragrances. Additives such as clays, mica and silica gel which retain water can also be employed to retain water as energy susceptors. Although wood contains natural antimicrobials, addition of antimicrobials such as Alphasan® can be employed to improve the composite performance.

It can be envisaged that the composites revealed herein can be compounded on conventional equipment such as two roll mill and extrusion. Likewise moulding can be carried out using compression, transfer or injection moulding and related techniques.

Another application of this system is in the arts and crafts, toys and prototyping. Since the material can become pliable via microwave radiation or through conventional heating techniques it makes a good moulding compound that can be handled comfortably and safely, particularly by children. After shaping or casting it cools to form rigid structure. The fillers can also provide an aesthetic value to the composite.

In one embodiment the present invention relates to a radiation activated moulding article comprising a novel thermoplastic composite, and a technique for producing the same. The article revealed can be activated via conventional heating or microwave radiation. The invention can be used for example in an orthopaedic splint or cast. On activation the thermoplastic composite becomes soft and drape like allowing the user to work the article into the required shape. On cooling the article forms a rigid cast preserving its shape throughout its lifetime.

When conventional thermoplastic materials are heated above melting temperature, they no longer retain their structural integrity and behave in a similar manner to that of a high viscosity liquid. In this invention, lignocellulosic materials, such as wood fibres; control the melt viscosity of polycaprolactone such that it retains sufficient melt strength and therefore its integrity. This allows the user to shape the heated material without it 'overspreading'. It is thus easier to arrange the flexible composite material in a desired location and/or orientation around an object to be moulded or shaped. The use of wood flower and/or wood fibre greatly reduces the tack of the activated composite. This is especially important where shaping or moulding is carried out manually as in the case of splints and casts.

Wood fibres also allow the control of the composite density as the wood fibres are compressible. By varying the pressures involved in manufacturing the product, it is possible to vary the free space from foam like cellular composites to high density composites.

The presence of fibrous material within the polycaprolactone matrix improves both the strength and creep resistance of the composite material. The material is not prone to cracking under impact unlike conventional moulding materials such as Plaster of Paris and synthetic resins.

The addition of wood fibres/flower to polycaprolactone generates a material which has a natural look, which for example used as a splint, forms an aesthetically pleasing yet discrete product. In addition lignocellulose materials alter the wettability characteristics of the polycaprolactone such that it is easily coated. In one case the composite material may be coated with a PVDC emulsion, which produces a smooth glossy skin.

Foaming of the composite material is also possible by the addition of foaming agents in the composite material (e.g. Water). Doping of the foaming agents with suitable microwave irradiation absorbers (susceptors) ensure that the foaming agents heat rapidly when exposed to microwave irradiation and thereby expand inside the softened composite material to produce a cellular structure throughout.

As both polycaprolactone and wood are biodegradable materials, by using wood as the additive material this ensures that the composite material is an environmentally-friendly material. Wood fibres, such as sawdust, used as the additive material, are an economical and widely-available resource. Under incineration polycaprolactone produces $CO_2$ and $H_2O$.

The combination of wood fibres and a low melt temperature thermoplastic provides the ability to incorporate a natural microwave susceptor, such as water. By compounding and processing the composite below 100° C., the wood fibres can be pre-hydrated and steam generation in the extruder process may therefore be eliminated. This is an important characteristic since moisture within the matrix acts as a microwave susceptor and heat distributor. This also has the potential for in-situ foaming where water acts as the foaming agent within the thermoplastic.

Application areas of the invention include braces, splinting fixation and casting bandaging for orthopaedic applications, custom moulded seating, handles and grips, degradable cutlery, protective padding such a shin guards for humans or animals, foot orthotics, braces and support for ulcerated foot conditions, hip protectors.

Advantages of using lignocellulosic materials such as wood for filled polycaprolactone include:

Lignocellulosic materials are a cheap, low cost material.
The lignocellulosic materials bulk up the polycaprolactone.
Lignocellulosic materials are a natural material.
Aesthetic appeal is enhanced by using lignocellulosic materials.
Lignocellulosic materials are degradable/disposable.
Lignocellulosic materials are an environmentally friendly solution. Using waste lignocellulosic materials results in a renewable material source.
Lignocellulosic materials enhance the strength/rigidity of the polycaprolactone.
Lignocellulosic materials enhance the creep resistance of the polycaprolactone.
Lignocellulosic materials improve the melt strength of the polycaprolactone.
Lignocellulosic materials improve the thermal conductivity of the polycaprolactone.
Lignocellulosic materials improve the surface finish, in particular it improves wettability and the adhesion for coating.
Lignocellulosic materials reduce the tackiness of the polycaprolactone.
Lignocellulosic materials can control the density/weight of the polycaprolactone.
Lignocellulosic materials can in some cases improve the foaming of the polycaprolactone.
Lignocellulosic materials result in extra extensibility of the polycaprolactone, when in a flexible state.
The resultant material is more compliable similar to a clay.
Conventional injection moulding techniques may be used to manufacture.
Conventional compounding techniques may be used for mixing and blending.
Lignocellulosic materials may provide a greater moisture content. Fragrances may be added to the lignocellulosic materials fibres.
For microwave heating, the lignocellulosic materials provide natural moisture susceptors integrated into the material.
Hydrated lignocellulosic materials improve the heating capabilities. Water is a thermal conductor.
Lignocellulosic materials improve the microwave heating of the composite. When heated in a sealed pouch or packaging, moisture released from the lignocellulosic materials fibres result in a more uniformly heated product i.e. reduces problems associated with "Hot and Cold" spots associated with microwave heating.
The edges of the material are rounded by the shearing action of a scissors and are therefore more safe for the wearer (compared to Plaster of Paris or Synthetic Casts).
No dust is emitted when the material/product is trimmed by a scissors (compared to Plaster of Paris or Synthetic Casts.) and there are low dust emissions when cut with a cast saw (compared to Plaster of Paris or Synthetic Casts.)
The product/material does not deteriorate or become heavier when the product is wet.
The matrix is radiolucent.
Material may be moulded in diamond matrix format.
Antimicrobial agents may be added to the material.
Composite material can be incinerated without the release of toxins.
No dust is emitted from the material when cut by a shears or scissors.
The composite materials revealed herein are not prone to degradation in water and the properties do not deteriorate in humid conditions.

Advantages of the diamond matrix structure of the wood filled polycaprolactone include:

The diamond matrix is conformable, pliable, stretchable and compressible.
The application process is easy and fast to apply, and is a dry process.
The diamond matrix is light weight, and the strength to weight ratio is good.
The diamond matrix is rigid, and easy to manufacture.
The diamond matrix reduces conditions conducive to bacteria growth and risk of infection (particularly in hot humid climates), reduces risk of skin maceration and irritation (particularly in hot humid climates), reduces conditions that give rise to excessive skin itch (particularly in hot humid climates), facilitates skin and underlying wounds to breath and speed up healing, and the diamond mesh structure enables wearer to scratch local itchy sites.
The matrix facilitates fast drying of a limb after immersion in water, and is suitable for swimming particularly for children.

Uncomfortable spots may be post-moulded locally using a hair dryer, after reduction of swelling casts may be remoulded locally using a hair dryer to make the cast snug fitting.

The diamond matrix facilitates construction of a hybrid full cast, whereby a back slab of the invention is covered with a standard synthetic resin cast (after the reduction of swelling). This reduces the risk of bone displacement and reduces material costs.

Diamond matrix is strong when moulded in an arc configuration e.g. around a limb Lamination of the spacer fabric, non wovens, foams and bandages from natural & manmade materials to a preformed splint product with a diamond matrix configuration is easy to manufacture and makes medical procedures fast and easy. (This is not possible with Plaster of Paris).

The diamond matrix configuration provides good shock dispersion properties.

There is no risk of material fracture or cracking due to stress or shock compared to Plaster of Paris or synthetic casts.

Another novelty relating to the disclosed technologies reveals a technique with which the packaging or coating improves the microwave heating of the underling mouldable material. Polymeric species with suitable polar molecular sequences such as ester linkages absorb microwave energy and convert it to thermal energy (e.g. polyester urethanes). It should also be noted that such films or coatings can be doped with susceptors to improve these characteristics.

BRIEF DESCRIPTION OF THE DRAWINGS

The invention will be more clearly understood from the following description of some embodiments thereof, given by way of example only, with reference to the accompanying drawings, in which:—

FIG. 2 is a plan view of a sample T bar splint device according to the invention, prior to application, suitable to be used for the support of a wrist or distal radial fracture;

FIG. 3 shows a cut section through the radial T bar splint device through the line XX, as shown in FIG. 2;

FIG. 20 is a plan view of a further splint device according to the invention;

FIG. 21 is a side view of the splint device of FIG. 20;

FIG. 22 is a perspective view of another splint device according to the invention;

DETAILED DESCRIPTION OF THE INVENTION

The term protective and/or splint device employed herein refers to a component, which may be preformed, and is used for limb immobilisation, support and/or protection. The term protective and/or splint device will be understood to include splints, casts, braces, and body protection for humans or animals. Such a protective and/or splint device may be used as an orthopaedic device or as an occupational-therapeutic device, or as a splint guard. The device may be used for humans or animals. Examples of protective and/or splint devices include hip protectors, shin guards, braces for use with a fractured bone.

In the examples given herein the primary low-melt thermoplastic material used is CAPA® 6500, which was supplied by Solvay UK. CAPA® 6500 is a high molecular weight linear polyester derived from caprolactone monomer. It has a molecular weight of approximately 50,000, and is supplied in granular form. It is compatible with a wide range of common thermoplastics, and soluble in several common solvents. It has a melt temperature of 57-59° C. making it an ideal suitable material for splinting applications where the heated product does not cause patient discomfort. The mechanical strength of the wood composites produced from such suggests that polycaprolactones wet wood fibres well during mixing.

Those skilled in polymer formulations will appreciate that a range of suitable systems exist which portray the required properties of the thermoplastics referred to herein. Materials such as EVA, low melt polyolefins, waxes and blends such as polycaprolactone/PVC and copolymers. A wide range of suitable materials can be found under the technology of non-reactive hot melt adhesives.

Figure 1:
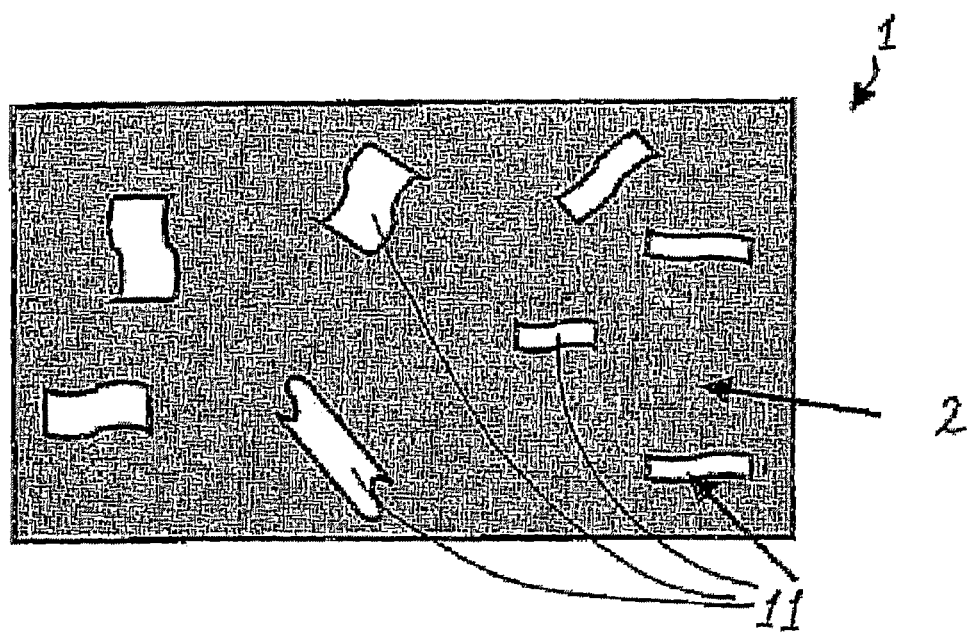
FIG. 1 is a schematic, cut-away illustration of a composite splint material according to the invention.

Referring to the drawings, and initially to FIG. 1 thereof, there is illustrated a fibre composite splint material 1 according to the invention. The composite splint material 1 is formable at a forming temperature above ambient temperature, and is substantially rigid at ambient temperature. The composite material 1 is thus particularly suitable for use in moulding applications, such as splinting. At the forming temperature, the composite splint material 1 may be formed and arranged into a desired location and/or orientation around an object to be splinted, such as a forearm having a fractured bone. At ambient temperature, the rigid composite material 1 may then act as a splint for the forearm.

The composite material 1 comprises a low-melt thermoplastic co-polymer, in this case polycaprolactone 2, and a plurality of fibres 11 of an additive material dispersed throughout the polycaprolactone 2. In this case, the additive material comprises a ligno-cellulose material, such as wood. Wood is a water-retaining material. Thus using wood as the additive material ensures that water may be retained within the composite material 1.

The material forming temperature is above 35° C., preferably above 50° C., and in this case is above 57° C.

FIG. 1 is a schematic view of the heatable thermoplastic composite 1. The polycaprolactone matrix 2 contains the hydroscopic wood fillers 11 which can be heated using microwaves.

Figure 4:
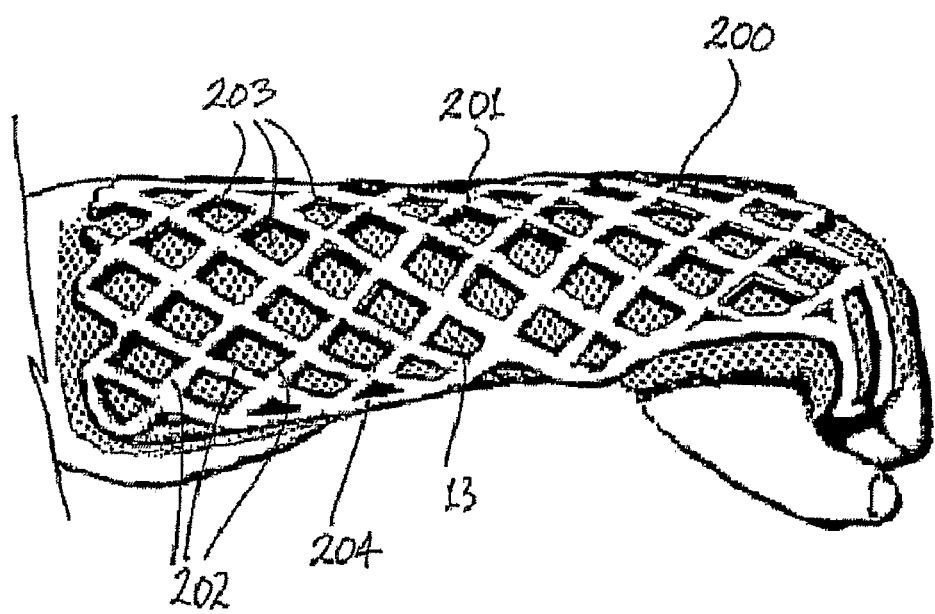
FIG. 4 is a perspective view of the splint device of FIG. 2 following application to a limb.

Referring to FIGS. 2 to 4 there is illustrated a distal radial splint device 200 according to the invention. The splint device 200 comprises a compression moulded splint member 201 and a spacer member 13. The splint member 201 comprises the composite splint material 1, as described previously with reference to FIG. 1. Thus the splint member 201 is formable at the forming temperature and is substantially rigid at ambient temperature.

As illustrated in FIG. 4, the splint member 201 is configured to extend around only a part of the limb being splinted.

The splint member 201 comprises a mesh of splint elements 202, with a plurality of openings 203 through the splint member 201. Away from the periphery of the splint member 201, the openings 203 are diamond-shaped, as illustrated in FIG. 2. Two border elements 204 extend along the two sides of the periphery of the splint member 201. Some of the openings 203 adjacent to the periphery of the splint member 201 are non diamond-shaped, as illustrated in FIG. 2.

Figure 5:
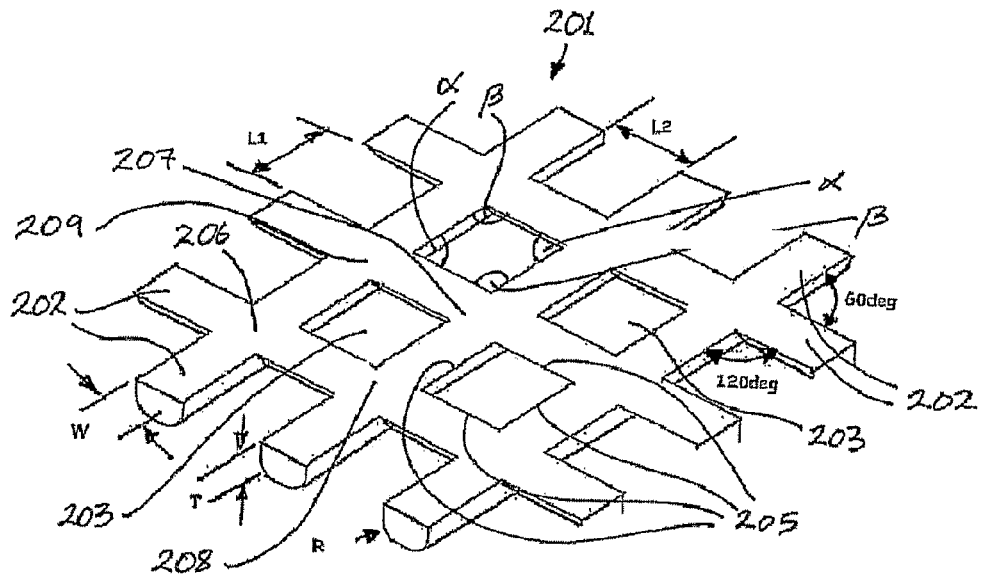
FIG. 5 is an isometric view of a preferred embodiment of a splint member of the splint device of FIG. 2.

As illustrated in FIG. 5, the mesh of splint elements 202 have four straight edges 205 around each diamond-shaped opening 203. The edges 205 define two acute angles α opposing one another and two obtuse angles β opposing one another. Each acute angle α is in the range of from 15° to 85° and in this example is 60°. Each obtuse angle β is in the range of from 95° to 175°, and in this example is 120°.

Figure 6:
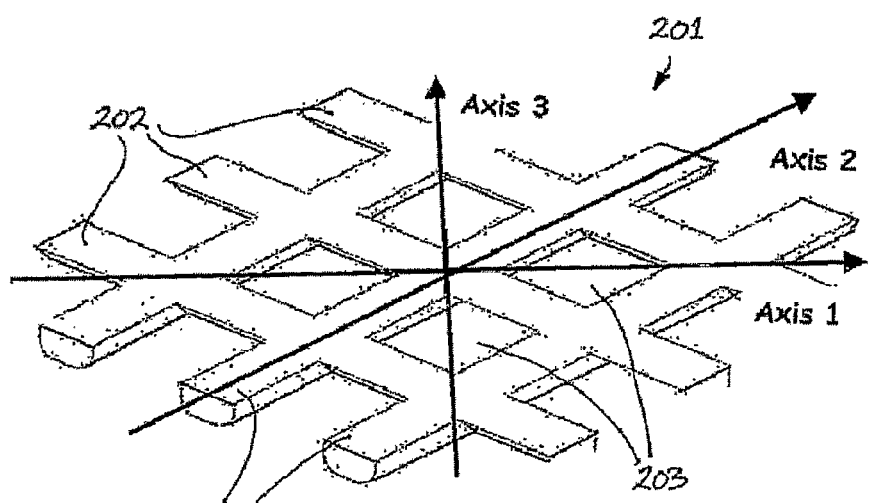
FIG. 6 is a view similar to FIG. 5 showing the axes used to define the bending characteristics of the splint member.

As illustrated in FIG. 6, the Axis 1 passes through the apex of the two acute angles α, and the Axis 3 passes through the apex of the two obtuse angles β. Axis 1, which is the longitudinal axis of the device 200, is orthogonal to Axis 2, which is the circumferential axis of the device 200. At ambient temperature, the flexural strength of the splint member 201 in a direction parallel to Axis 1 is greater than the flexural strength of the splint member 201 in a direction parallel to Axis 3. The flexural strength of the splint member 201 in the direction parallel to Axis 3 may be in the range of from 10% to 90% of the flexural strength of the splint member 201 in the direction parallel to Axis 1, and is preferably in the range of from 20% to 80% of the flexural strength of the splint member 201 in the direction parallel to Axis 1.

Between each pair of adjacent openings 203, the splint member 201 comprises a junction. For each opening 203, the splint member 201 comprises a first junction 206 on one side of the opening 203, a second junction 207 on an opposite side of the opening 203 to the first junction 206, a third junction 208 on another side of the opening 203, and a fourth junction 209 on an opposite side of the opening 203 to the third junction 208. As illustrated in FIGS. 5 and 6, the distance between the first junction 206 and the second junction 207 is greater than the distance between the third junction 208 and the fourth junction 209. As illustrated in FIG. 6, Axis 1 passes through the first junction 206 and the second junction 207, and Axis 3 passes through the third junction 208 and the fourth junction 209.

At the forming temperature, the splint member 201 is stretchable in both the direction parallel to Axis 1 and in the direction parallel to Axis 3. By stretching the splint member 201 in this manner, the splint member 201 may be formed and arranged around an object to be splinted.

As illustrated in FIG. 3, the splint member 201 comprises an outer surface 210 for facing away from an object being splinted and an inner surface 211 for facing towards the object being splinted.

The splint member 201 is rounded between the outer surface 210, and each of the edges 205 around each of the openings 203. The splint member 201 is also rounded between the outer surface 210 and each of the side edges 212 around the periphery of the splint member 201.

The splint member 201 comprises a corner, in this case a 90° corner, between the inner surface 211 and each of the edges 205 around each of the openings 203. The splint member 201 also comprises a corner, in this case a 90° corner, between the inner surface 211 and each of the side edges 212 around the periphery of the splint member 201.

In this case the cross-sectional profile of the splint member 201 is constant over the splint member 201.

The percentage of the total cross-sectional area of the openings 203 to the total cross-sectional area of the splint member 201 may be in the range of from 1% to 80%, preferably in the range of from 10% to 60%, and most preferably in the range of from 15% to 50%.

The spacer member 13 may comprise of a foam or a padding bandage, and the spacer member 13 is configured to be located between the splint member 201 and the object being splinted (FIG. 4).

In use, the splint device 200 is heated, for example by convectional heating, from ambient temperature to the forming temperature. At the forming temperature the splint member 201 is relatively flexible. The splint device 200 may thus be formed and arranged into a desired location and/or orientation around the object to be covered.

The device 200 is then allowed to cool to ambient temperature while remaining in the desired splinting location and/or orientation around the object. At ambient temperature the splint member 201 is rigid. The now rigid device 200 maintains the object splinted in the desired location and/or orientation.

FIG. 2 shows a plan view of the un-activated radial T bar splint member 201 juxtaposition to the padding fabric 13 which is fixed to the splint member underside 211. The splint member 201 is preformed using moulding techniques and therefore the splint member 201 contains no sharp edges, as would possibly be obtained from extrusion or die cutting processes. In this example, the apertures 203 are aligned such that the splint device 200 provides maximum flexural rigidity at a slight angle to the axis of the bone. This allows the apertures 203 to align with the geometry of the knuckles and therefore provide maximum limb support and snugness of fit. The padding material 13 may be a closed cell foam with punched openings. A suitable padding material is disclosed in U.S. Pat. No. 4,294,240. The splint member 13 allows for breathing in three dimensions and dries efficiently to maximise patient comfort. Ideally the padding 13 will have low drape resistance and allow for fast and efficient water removal in order to optimise the use of the device openings 203.

FIG. 3 is a cut section through the line XX of the radial T bar splint device 200 shown in FIG. 2. The splint liner/padding 13 is on the underside 211 of the splint member 201.

FIG. 4 is an isometric view of the radial backslab splint device 200 of FIG. 2 following activation and application to the lower arm. For visual purposes no strapping is shown. However it will be appreciated that a wide range of wrapping and strapping could be employed for such including Velcro, crepe bandages, adhesive tapes etc.

The splint member 201 may be activated using dry heat, such as a conventional oven, or microwave heating. In this situation the user does not come into contact with water and the padding 13 remains dry. The splint member 201 may also be activated in heated water. Since the splint device 200 is very open, it is believed that drying will be efficient and therefore there is little concern regarding the wetting of the underlying padding 13. In the case where water activation is used, the splint member 201 and the padding 13 may be supplied separately and combined after the splint member activation.

We have found that when lignocellulose additive material 11 was loaded in quantities above 15 wt % into CAPA6500®, the handling of the activated material 1 became much easier with very little tack. The filler 11 also reduces the polymer elastic properties, and the material 1 drapes like a wet fabric making it easy to shape to the limb.

Referring to FIG. 5, an isometric view of the mesh splint member 201 of the splint device 200 shows a criss-cross series of ribs 202 which network to form a continuous plaque. The ribbed elements 202 are presented as channels of thickness T, where thickness is in the range of 0.2 mm to 10 mm, preferably 3 mm to 8 mm, and most preferably 4 mm to 7 mm. The channel width W is interrelated to the overall system openness and is in the range of 2-12 mm, preferably 4-10 mm. The opening geometry is defined by the length L1, the length L2, and the element angles α, β, where the lengths L1, L2 range from 2-25 mm, preferably from 5 to 18 mm. The rib angles α, β determine the anisotropic levels within the splint member 201 and are in the range from 15° to 175°, more preferably 30°-150°. Along with the material characteristics, all of these parameters may be varied to define the mechanical characteristics, openness, apertures per unit area, weight and anisotropic characteristics of the splint member 201.

FIG. 6 is another isometric view of the mesh splint member 201 defining a series of axes A1, A2, A3 across the mesh plaque. These axes are used in the example section below where the anisotropic characteristics of the splint member 201 are discussed in further detail. Axis 1 passes through the widest part of the diamond apertures 203 and it has been found that in most cases, this Axis 1 is the axis of highest flexural strength and therefore is the axis most suitable to run parallel to the bone. Axis 3 passes through the shortest points of the diamond openings 203 and therefore it is beneficial to have this Axis 3 perpendicular to the bone allowing for maximum give during swelling and adjustment of the bracing systems. It should be appreciated that the geometry of a diamond is not the only opening geometry which can be applied to produce such anisotropic effects, see for example FIGS. 9 to 14 below. However we have chosen the diamond-shaped openings 203 for illustration and to help explain the disclosures herein.

Figure 7:
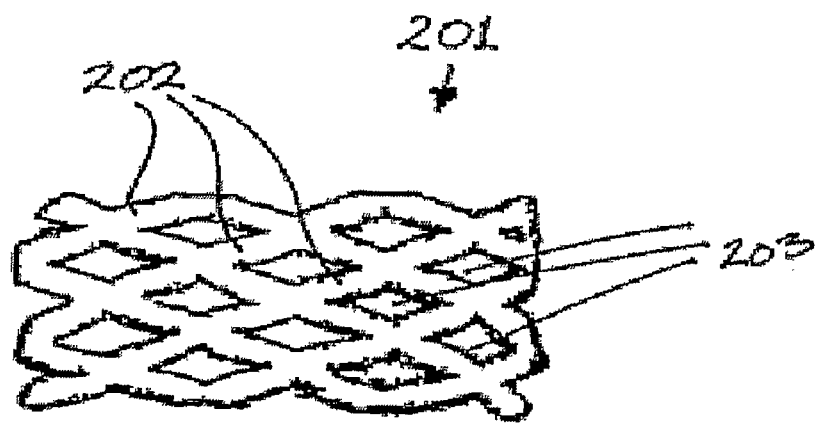
FIG. 7 is a plan view of the mesh splint member of FIG. 5 prior to activation.
Figure 8:
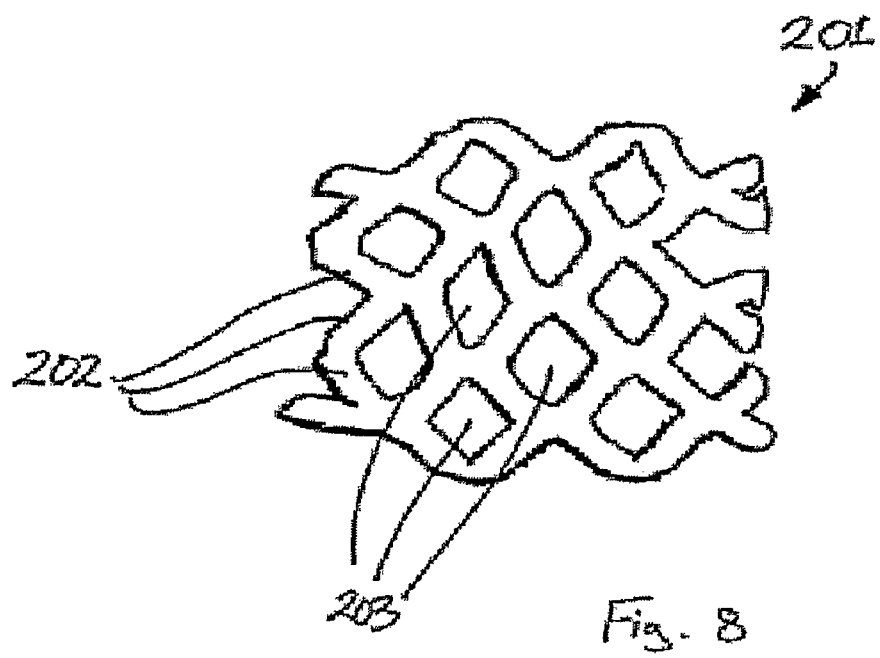
FIG. 8 is a plan view of the mesh splint member of FIG. 5 following activation and stretching.

FIGS. 7 and 8 show a plan of the mesh plaque splint member 201 prior to activation, and following activation and stretching respectively. The plaque 201 shown in FIG. 8 has been stretched over 25% of its original length without any significant reduction in element thickness and therefore the strength is maintained. This function allows splint devices to be designed with larger size ranges and therefore reduces product inventory. In addition this stretching allows the user to re-distribute the product strengths in different orientations.

Figure 9:
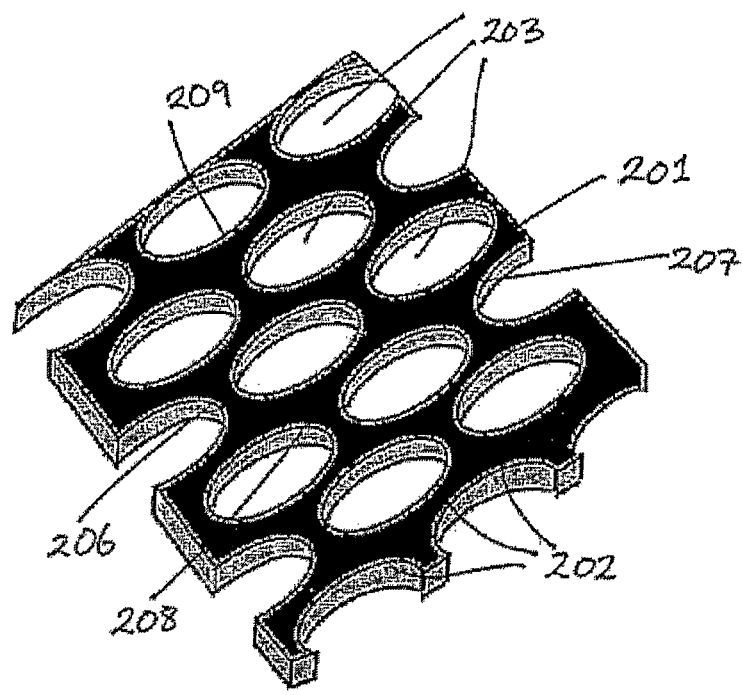
FIG. 9 is a member of an alternative device according to the invention where the sheet elements intertwine to form oval apertures.

FIG. 9 is an alternative embodiment of the splint member 201 to the diamond-shaped mesh geometry shown in FIGS. 2 to 8. In this embodiment the mesh elements 202 are joined to produce elliptical openings 203. When this geometry is employed it portrays the anisotropic splint characteristics.

Figure 10:
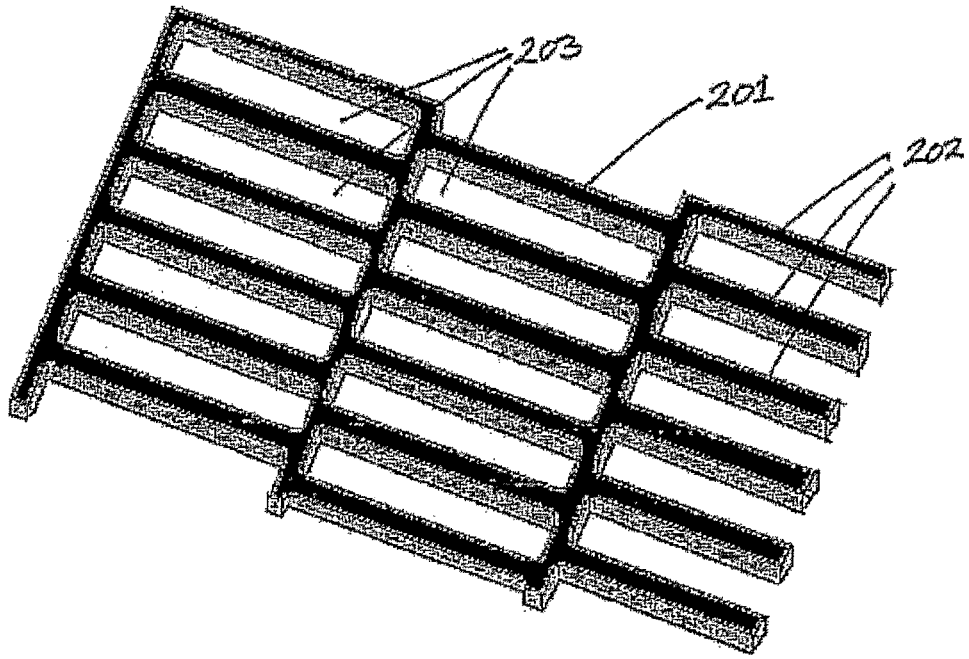
FIG. 10 is a member of an alternative device according to the invention where the sheet elements intertwine to form rectangular openings.
Figure 11:
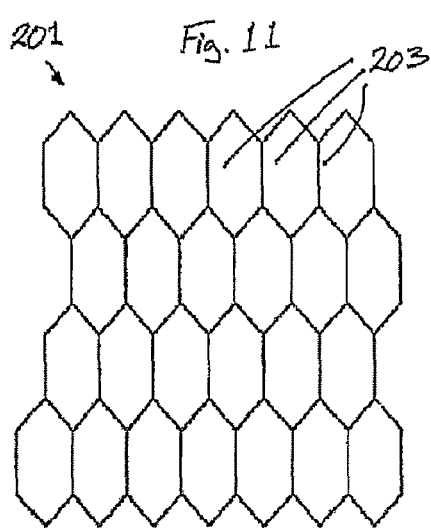
FIGS. 11 to 14 are plan views of splint members of other splint devices according to the invention.
Figure 12:
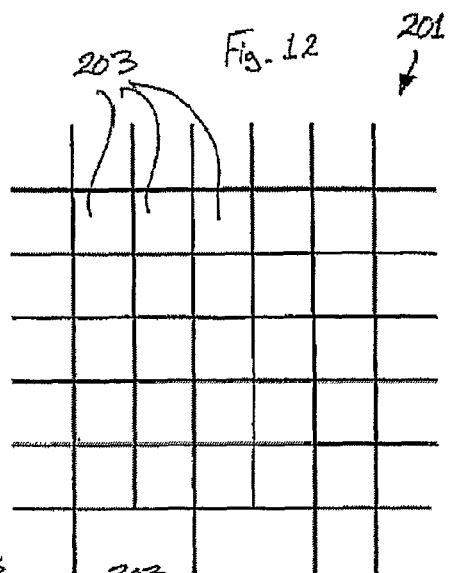
Figure 13:
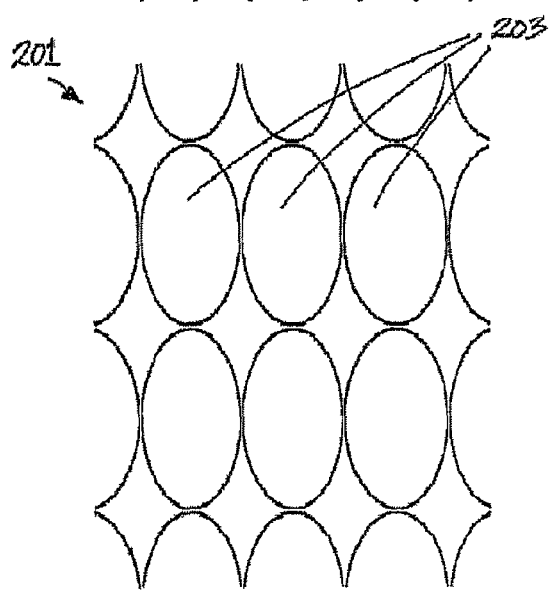
Figure 14:
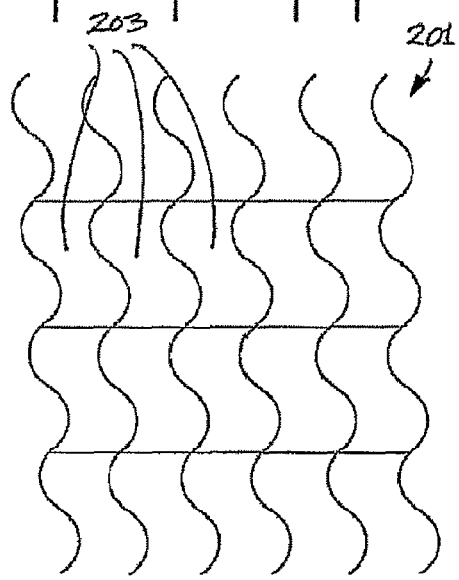

FIG. 10 is a grid-like splint member 201 in which the mesh elements 202 are joined to produce a splint member 201 with rectangular openings 203.

FIGS. 11 to 14 illustrate other possible design configurations for the splint member 201, such as hexagonal openings 203 (FIG. 11), square openings 203 (FIG. 12), S-shaped openings 203 (FIG. 14), star-shaped openings. Another particularly suitable configuration is a parallelogram-shaped or parallelepiped opening 203. It will be appreciated that the invention is not limited or restricted to only diamond-shaped openings 203.

Different configurations for the openings 203 allow the flexibility of the splint member 201 to be varied without changing the material formulation. For example different configurations for the openings 203 may be advantageous or particularly suitable for splinting different parts of the body.

Figure 15:
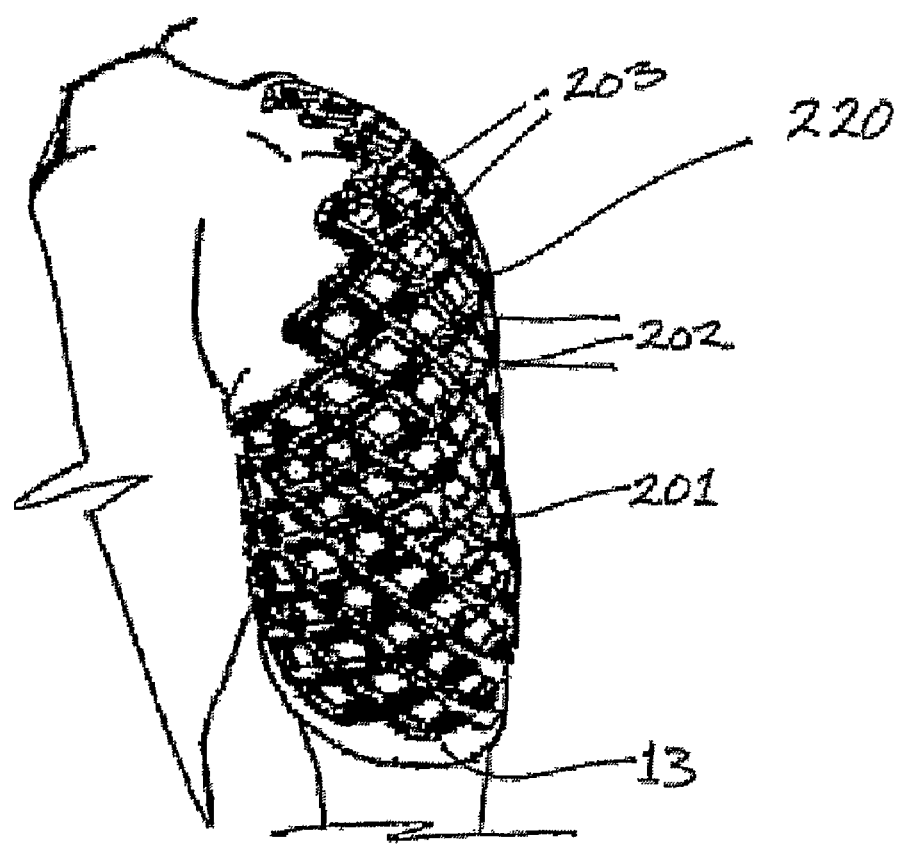
FIG. 15 is a perspective view of a splint device according to the invention for supporting the proximal mid-humerus section of an upper limb employing the embodiment of the current invention.

FIG. 15 illustrates another splint device 220 according to the invention, which is similar to the splint device 200 of FIGS. 2 to 8, and similar elements in FIG. 15 are assigned the same reference numerals.

In this case the splint device 220 is a mid-humerus brace, and FIG. 15 illustrates the moulded humeral splint brace 220. The brace device 220 is shown on the limb following activation and moulding.

Figure 16:
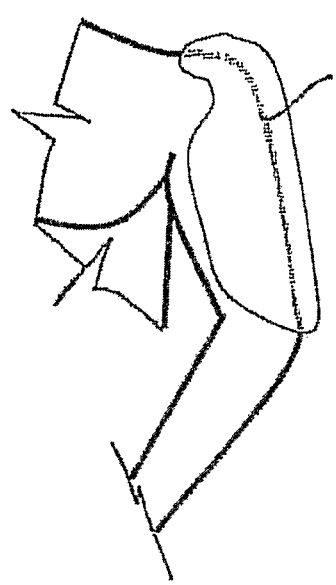
FIG. 16 is a plan view of another splint device according to the invention.
Figure 17:
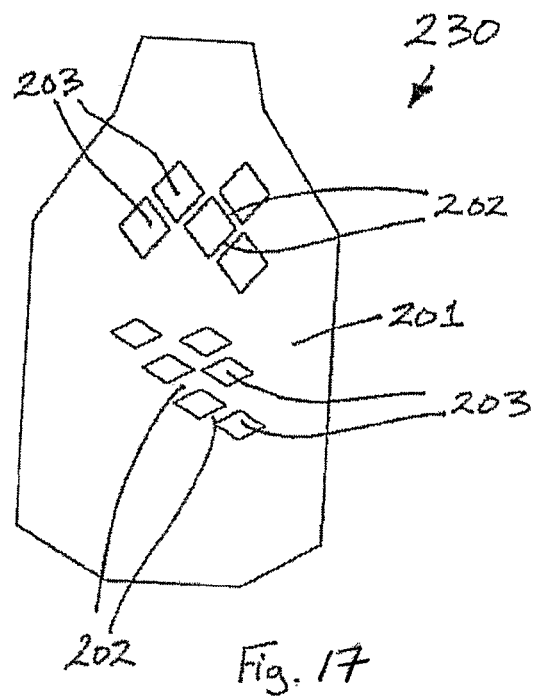
FIG. 17 is a perspective view of the splint device of FIG. 16, in use.

In FIGS. 16 and 17 there is illustrated another splint device 230 according to the invention, which is similar to the splint device 220 of FIG. 15, and similar elements in FIGS. 16 and 17 are assigned the same reference numerals.

In this case, the size of the openings 203 and the number of openings 203 per $cm^2$ varies over the splint member 201.

FIGS. 16 and 17 illustrate the mid humerus brace device 230 with the diamond variation. The variation allows for stretching/strength gradients in the splint device 230. This facilitates sizing of the device 230 during moulding around the shoulder area and lower humerus.

Figure 18:
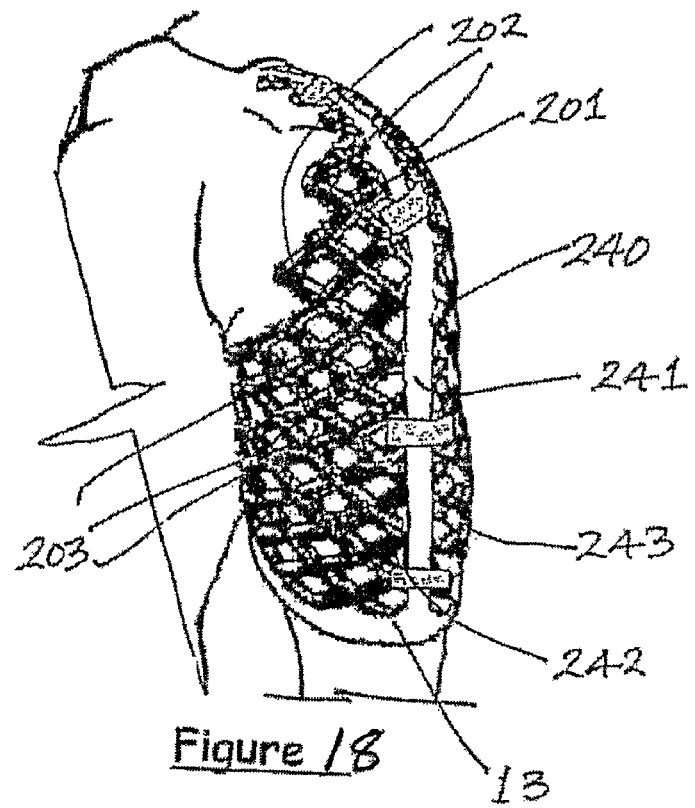
FIG. 18 is another splint device according to the invention which contains a hinge allowing for easy adjustment and removal of the splint device.

In FIG. 18 a further splint device 240 according to the invention is illustrated, which is similar to the splint device 220 of FIG. 15, and similar elements in FIG. 18 are assigned the same reference numerals.

In this case a hinge system 241 is incorporated to allow easy removal and adjustment of the humeral splint device 240. In this design the mesh elements 202 are provided in the form of two components 242, 243 with a fabric bridge 241 allowing one mesh component 242 to move relative to the other 243.

Figure 19:
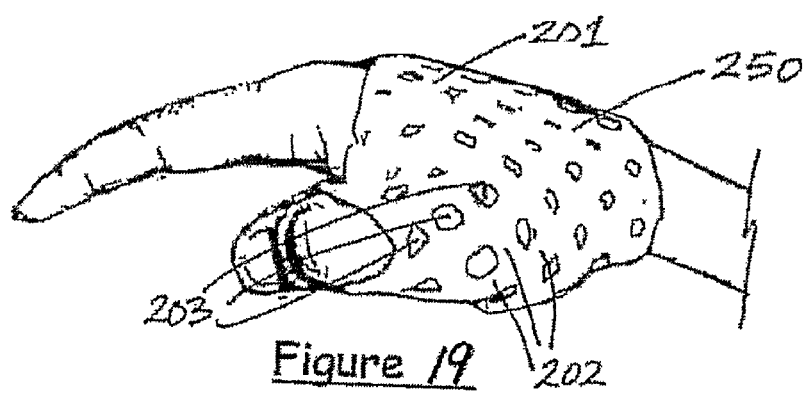
FIG. 19 is a perspective view of a hand protection device according to the invention.

Referring to FIG. 19 there is illustrated a further device 250 according to the invention, which is similar to the device 200 of FIGS. 2 to 8, and similar elements in FIG. 21 are assigned the same reference numerals. The device 250 is a hand protector with diamond openings.

FIGS. 30 and 31 illustrate another splint device 300 according to the invention, which is similar to the splint device 200 of FIGS. 2 to 8.

In this case the splint device 300 comprises a first splint member 301 and a second splint member 302 jointed by a series of ribs 110. The ribs 110 may be broken/cut to facilitate movement of the first splint member 301 relative to the second splint member 302. The "shark teeth" ribs 110 of FIGS. 20 and 21 allow for a dynamisable splint—Reflex Sympathetic Dystrophy (RSD). The sacrificial ribs 110 are provided to enable the hinging of the splint device 300.

In FIG. 22 a further splint device 310 according to the invention is illustrated, which is similar to the splint device 300 of FIGS. 20 and 21, and similar elements in FIG. 22 are assigned the same reference numerals.

In this case a hinge joint 311 is provided between the first splint member 301 and the second splint member 302 to facilitate movement of the first splint member 301 relative to the second splint member 302. The splint device 310 of FIG. 22 allows for a dynamisable forearm splint-reflex sympathetic dystrophy. The splint device 310 allows for motion treatment on one axis to improve healing.

An important requirement for a splint device is to support and maintain bone alignment around the fracture site. The splint device of the invention achieves support without having any substantial product weight increase. According to the invention a splint device has been devised where both the resistance to bending and the openness of the splint device have been optimised. The high level of openness allows the splint device to be thicker with a minimum increase in splint weight per unit area, and thus minimise the increase in the second moment of area.

The invention provides in one case a splint device comprising a moulded foraminous plaque supplied in the form of a flat pre-sized component useful as, for example, an orthopaedic immobilisation or body protection device. On heating to the forming temperature, the splint member material exhibits a thermal transition allowing it to become formable and shapeable by hand and therefore moulded, for example, around a limb. On cooling the splint member rigidities again to match the limb contours. The splint device of the invention provides excellent support to the wearer with a large open area to provide ventilation to the underlying surface.

Figure 23:
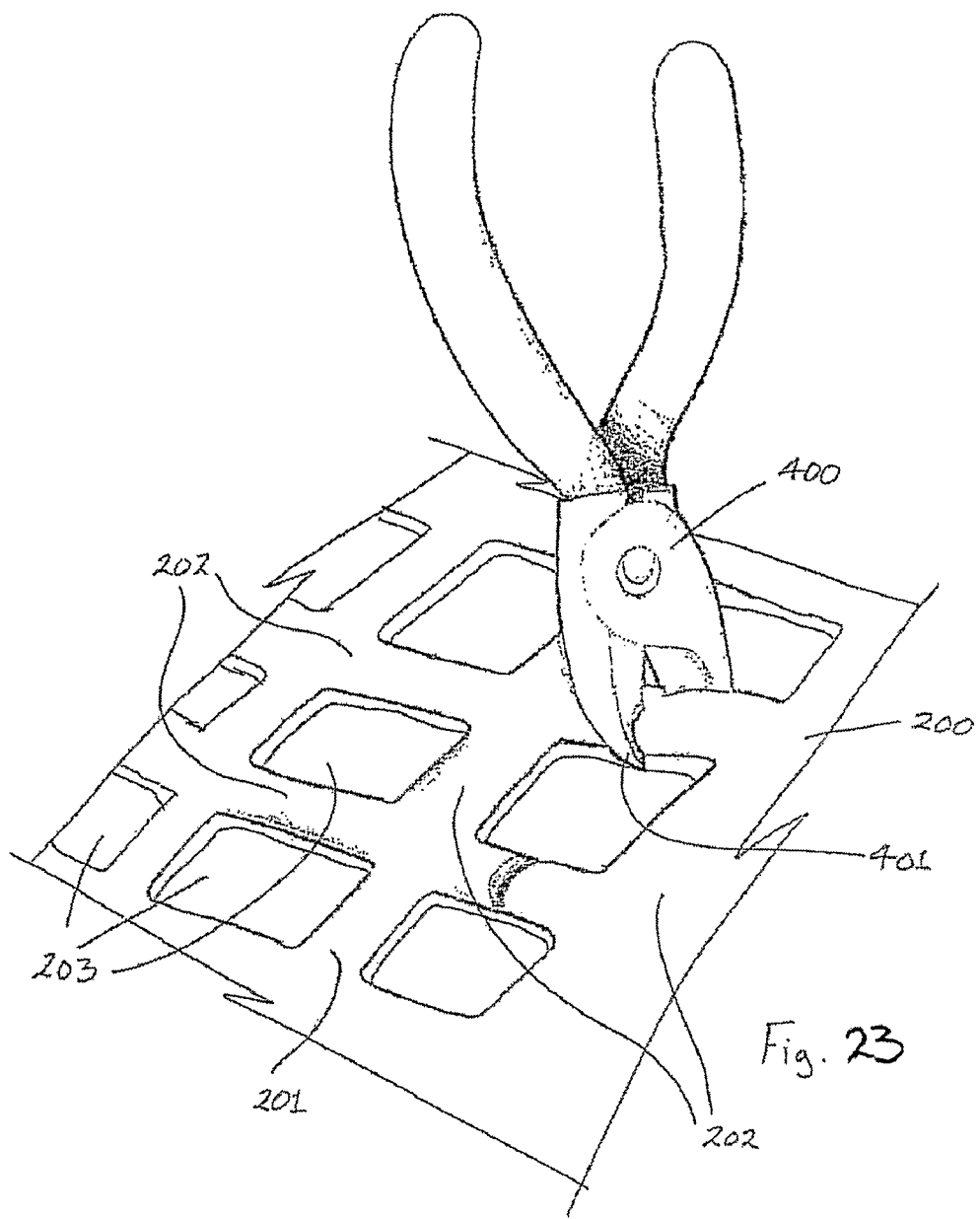
FIG. 23 is a perspective view illustrating removal of the splint device of FIG. 2.

The splint device 200 of the invention facilitates easy removal from a patient without the necessity to use a cast saw. As illustrated in FIG. 23, this is achieved by means of the geometry of the splint device 200 which facilitates entry from directly above with a snips 400. The snips 400 slips under each rib of the splint member 201 and allows the user to cut off a full splint device 200 without risk of cutting or pinching the patient's skin. Also individual ribs can be removed using a snips in selected areas of the device to facilitate inspection monitoring or treatment or to permit entry through the device to facilitate indwelling devices, light treatments, probes, imaging, pharmaceuticals, gasses, injections, topical sprays, ultrasonic devices, electrical devices and circuitry, neuromuscular stimulation devices and percutaneous pinning.

This feature allows the device to be cut or trimmed without the necessity for power tools and with minimum noise. In turn there is minimum discomfort and stress to the patient and the risk to the patient is reduced. This feature also allows the splint to be removed using an inexpensive device in emergencies such as excessive odema or thrombosis. The person removing the device is not exposed to dust and therefore extraction is not necessary locally to capture dust and fibrous particles.

It will be appreciated that in an alternative embodiment of the invention, the cross-sectional profile of the splint member may vary over the splint member. Similarly in other embodiments the thickness of the splint member may vary over the splint member.

It will be appreciated that the composite splint material and the splint device of the invention are suitable for use in a wide variety of applications, for example in back supports, or in limb splints.

It should be noted that the examples shown in the Figs. and discussed herein are just part of a vast range of possible applications for immobilisation and support of limbs. Other possible areas of application include back support, body protection, etc. In addition the splint devices could be employed in a preformed state reducing the need for activation. Other applications include veterinary supports, protection devices, occupational therapy supports etc.

The invention is not limited to the embodiments hereinbefore described, with reference to the accompanying drawings, which may be varied in construction and detail.

EXAMPLES

Strength To Openness Ratio

Three alternative mouldable splint/cast materials (Plaster of Paris, Synthetic and Thermoplastic Mouldable Splints) were selected, examined and rated against the splint device of the invention.

Two test methods were developed to enable alternative mouldable splint/cast materials to be rated against the splint device of the invention.

The first test used was a 3 point flexural bending test method which was useful to establish the anisotropic flexural strength characteristics in different axes of the splint/cast materials tested.

A Unidirectional Bending Test Method was used to determine the average flexural strength characteristics of the alternative materials and the splint device in all axes simultaneously. The Unidirectional test method proved useful for testing devices with different geometrical apertures in order to give a single S:O index that covered the flexural strength characteristics in all axes of each device.

Three Point Flexural Bending Test

Sample Preparation Procedure A

The splint device of the invention was prepared in two stages. Stage one involved the preparation of the composite polymer splint material. This material was formed on a two-roll mill with roll temperatures of 95-115° C. Initially a weighed sample of virgin Polycaprolactone 6500® was added to the rollers and allowed to heat for 2 minutes. 33 wt % of Lignocel S150TR was added and mixing was carried out until an even blend dispersion was observed. The material was then removed from the heated roll with the knife edge.

The heated material was metered and then moulded in a compression moulding press using a flat Aluminium mould with diamond-shaped apertures at 30 tonnes pressure on a 500 mm×500 mm platen.

Sample Preparation Procedure B

Plaster of Paris and Synthetic samples were prepared as follows:

The material was trimmed to the required size prior to immersion into water. The pre-cut sections were then layered into various-ply laminates and immersed into lukewarm water for 3 seconds. The Plaster of Paris sample produced was 7-ply, the Synthetic sample produced was 4-ply. On removal the excess water was forced from between the laminate layers and the samples placed on a flat Teflon™-covered surface for 24 hours.

Sample Preparation Procedure C

The alternative thermoplastic samples for testing were trimmed to size using a sharp knife, then heated as per instructions for normal product usage and stored for 24 hours at room temperature before being tested. This was done to ensure that all samples tested represented as closely as possible the conditions specified by their respective manufactures during application of these devices in the field.

The splint device of the invention was cut to the correct size corresponding to the lateral axis of the limb.

Figure 24:
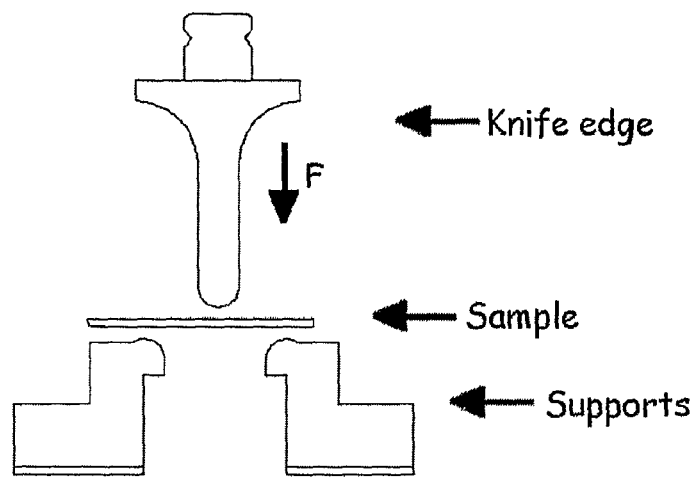
FIG. 24 is an illustration of a three point bending fixture used for S/O index determination.

Three-Point Bending Testing was carried out on a Zwick Universal Tensile Testing machine model Zwick Z2.5 using a three-point bending attachment. The width of the lower support jaws and upper knife-edge was 100 mm (See FIG. 24). The sample was placed centrally on the unit and the upper knife-edge was gradually brought into contact with the surface of the sample. The test was carried out at a rate of 25.00 mm/min and completed to a deflection level of 10 mm. The sample span length was 100 mm between the supporting knife edges. Therefore the effective area under test was 100 cm$^2$.

After the test was completed the volume of material in each 100 cm$^2$ test sample was measured and recorded. All inputs in the calculation were based on a 100 cm$^2$ sample.

The Strength to Openness Ratio Index (S:O Ratio Index) was calculated using the force required to produce a 10 mm deflection in three point bending, divided by the volume of material used, multiplied by the percentage of open area.

The S:O Index can be expressed by the following formula:

$$F/V \times \% \ OA = S{:}O \ \text{Index}$$

F=Force required (N) to deflect a 100 cm2 test sample by 10 mm

V=Volume of material (cm$^3$) used in the 100 cm$^2$ test sample

% OA=Percentage open area (%) of the 100 cm$^2$ test sample

The splint devices of the invention exhibited higher S:O index values than the alternative products in the comparison 3 point bending test. Therefore it can be anticipated that splint devices of the invention will have a higher performance-service rating in the field compared to the alternative products tested.

Unidirectional Bending Test

The splint device of the invention, plaster of Paris, synthetic and alternative thermoplastic samples were prepared using the same procedure as described in Sample Preparation Procedures A, B and C respectively.

NB: The sample size was 135 mm×135 mm.

Description of Unidirectional Bending Test:

The Unidirectional bending test was carried out on a Zwick Universal testing machine, model ZN 2.5 using unidirectional bending attachments ref fig (24) below:

A sample with dimensions 135 mm×135 mm was placed on the support element of the apparatus. This element has an inner diameter of 102.8 mm and an outer diameter of 122.8 and has a 5 mm radius edge; the area encapsulated by the rounded edge was effectively 100 cm$^2$.

A compression force was applied to the sample by the centre bending element. The bottom edge of the element has a 5 mm radius. The area enclosed by the centre bending element was effectively 20 cm$^2$.

TABLE I

Strength to Openness ratio of splinting systems using three point bending
3 Point Bending Results

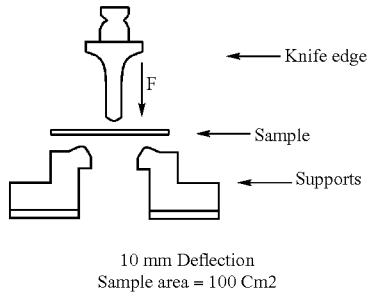

10 mm Deflection
Sample area = 100 Cm2

| Test No. | | Aperture Type | Rib width mm | % Openness | Thickness | Force (N) | V V (Cm3) used in sample | F/V Force/V | S/O Index (F/V) x Open Area |
|---|---|---|---|---|---|---|---|---|---|
| Splint Device of the invention |
| 1 | TPW | Symetrical Diamond | 6 | 42.0% | 4.8 | 114.6 | 23.66 | 4.844 | 2.035 |
| 2 | TPW | Symetrical Diamond | 8 | 36.0% | 5 | 192.1 | 27.20 | 7.062 | 2.542 |
| 3 | TPW | Symetrical Diamond | 8 | 13.0% | 3.2 | 75.7 | 23.66 | 3.200 | 0.416 |
| 4 | TPW | Symetrical Diamond | 8 | 19.0% | 2.4 | 29.8 | 16.52 | 1.805 | 0.343 |
| 5 | TPW | Symetrical Diamond | 8 | 33.5% | 5 | 204.0 | 28.25 | 7.222 | 2.421 |
| 6 | TPW | ASymetrical Diamond | 8 | 33.0% | 5 | 209.8 | 28.48 | 7.369 | 2.432 |
| Alternative Products |
| 7 | TP | Punched holes | na | 4.5% | 4.8 | 190.2 | 45.84 | 4.150 | 0.187 |
| 8 | TP | Punched holes | na | 19.0% | 3.2 | 34.6 | 25.92 | 1.336 | 0.254 |
| 9 | TP | Punched holes | na | 1.0% | 3.2 | 64.1 | 31.68 | 2.025 | 0.020 |
| 10 | TP | Punched holes | na | 1.0% | 3.2 | 69.8 | 31.68 | 2.204 | 0.022 |
| 11 | TP | Punched holes | na | 1.0% | 3.2 | 69.8 | 31.68 | 2.202 | 0.022 |
| 13 | POP | na | na | 0.1% | 6 | 48.5 | 59.94 | 0.810 | 0.001 |
| 14 | SYN | Minature openings | na | 1.5% | 4 | 154.9 | 39.400 | 3.932 | 0.059 |

TPW = Thermoplastic with 33 wt % Wood
TP = Thermoplastic
POP = Plaster of Paris
SYN = Synthetic Resin cast bandage
Note:
the openness of the Synthetic Bandage and Plaster of Paris samples were estimated as 0.1% and 1.5% respectively.

Brief Description of Test Method

A sample was placed centrally on the lower support element covering the contact edges. The central compression bending element was gradually lowered to the sample surface. The load was applied to the sample at a crosshead speed of 25 nm/min until 10 mm deflection was achieved (see FIG. 25). The applied force required to achieve this deflection was recorded. All inputs in the calculation were based on a 100 cm$^2$ sample.

The Strength to Openness Index (S:O Index) was calculated using the force required to produce a 10 mm deflection in unidirectional point bending, divided by the volume of material used, multiplied by the percentage of open surface area.

The S:O Index can be expressed by the following formula:

$$F/V \times \% \, OA = S:O \, \text{Index}$$

F=Force required (N) to deflect a 100 cm$^2$ test sample by 10 mm

V=Volume of material (cm$^3$) used in the 100 cm$^2$ test sample

% OA=The percentage open area (%) of the 100 cm$^2$ test sample help support the softened splint and hold it in place while cooling occurs. Again on cooling the packaging can be peeled away. Possible films for this application include flexible polyolefin's and thermoplastic polyurethane elastomers.

To reduce the likelihood of the apertures closing on application a filling component may be incorporated within the apertures. Following device application this filling component or plug can be removed. One approach is to employ a bubble-wrap covering over the outer surface of the splint where the bubbles align and fill the apertures. Following heating, application and device solidification the film containing the bubbles can be removed.

In the device of the invention the apertures are moulded, i.e. non-perforated. After initial manufacturing there is no subsequent material removal process required (no secondary process required).

This contrasts with alternative arrangements in which sheets with holes are die-cut, e.g. perforated/punched out of the sheet in a second process operation.

The invention claimed is:

1. A protective and/or splint device comprising a member formed from a composite material including a polycaprolac-

TABLE 2

Figure 25:
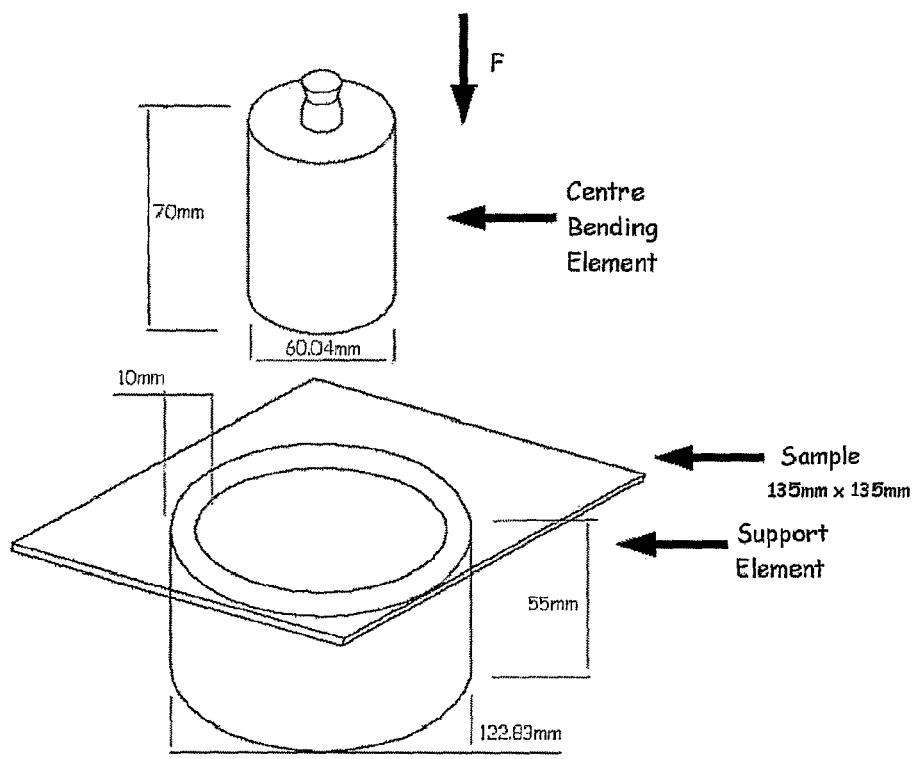
FIG. 25 is an illustration of a unidirectional bending fixture used for S/O index determination.
Figure 26:
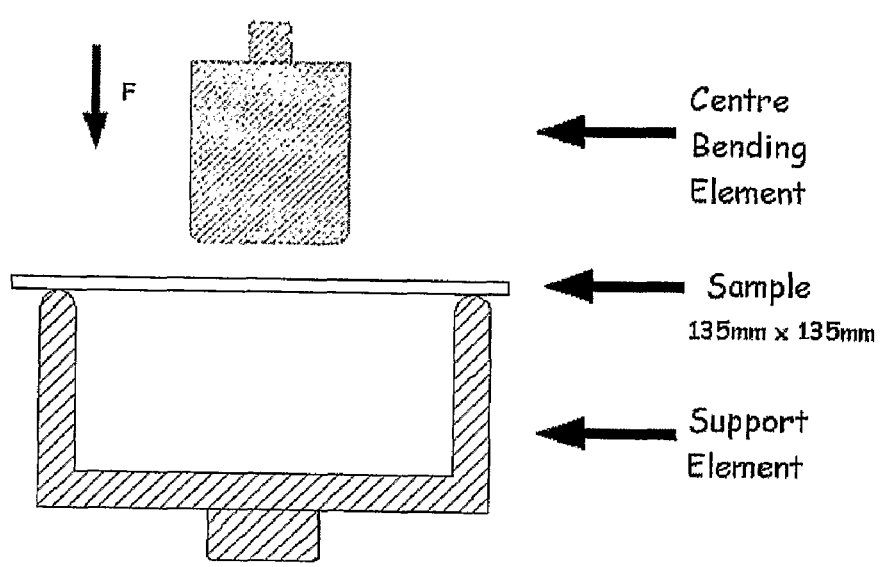
FIG. 26 is a cross-sectional view of the fixture shown in FIG. 25 used for S/O index determination.

Strength to Openness ratio of splinting systems using Unidirectional bending test
Uni-directional Strength to Openness Test Results
See Fig. 25 of the drawings
10 mm Deflection
Sample area = 100 Cm2

| Sample No. | Aperture Type | Rib width mm | % Openness | Thickness | Force (N) | V V (Cm3) used in sample | F/V Force/ V | S/O Index (F/V) x Open Area |
|---|---|---|---|---|---|---|---|---|
| Splint Device of the invention | | | | | | | | |
| 1 | TPW | Symmetrical Diamond | 6 | 42.0% | 4.8 | 525 | 23.66 | 22.196 | 9.322 |
| 2 | TPW | Symmetrical Diamond | 8 | 36.0% | 5 | 843 | 27.20 | 30.995 | 11.158 |
| 3 | TPW | Symmetrical Diamond | 8 | 13.0% | 3.2 | 1085 | 23.66 | 45.870 | 5.963 |
| 4 | TPW | Symmetrical Diamond | 8 | 19.0% | 2.4 | 599 | 16.52 | 36.243 | 6.886 |
| 5 | TPW | Symmetrical Diamond | 8 | 33.5% | 5 | 1022 | 28.25 | 36.172 | 12.125 |
| 6 | TPW | Asymmetrical Diamond | 8 | 33.0% | 5 | 746 | 28.48 | 26.210 | 8.649 |
| 7 | TP | Punched holes | na | 4.5% | 4.8 | 1714 | 45.84 | 37.392 | 1.683 |
| 8 | TP | Punched holes | na | 19.0% | 3.2 | 658 | 25.92 | 25.382 | 4.823 |
| 9 | TP | Punched holes | na | 1.0% | 3.2 | 960 | 31.68 | 30.307 | 0.303 |
| 10 | TP | Punched holes | na | 1.0% | 3.2 | 1233 | 31.68 | 38.923 | 0.389 |
| 11 | TP | Punched holes | na | 1.0% | 3.2 | 1118 | 31.68 | 35.284 | 0.353 |
| 13 | POP | na | na | 0.1% | 6 | 503 | 59.94 | 8.397 | 0.008 |
| 14 | SYN | Miniature openings | na | 1.5% | 4 | 563 | 39.40 | 14.301 | 0.215 |

TPW = Thermoplastic with 33 wt % Wood
TP = Thermoplastic
POP = Plaster of Paris
SYN = Synthetic Resin cast bandage
**Note:
Splint Device of the invention volumes are lower due to rounded profiles The splint devices of the invention exhibit higher S:O index values than the alternative products in the comparison unidirectional bending test. Therefore it can be anticipated that splint devices of the invention will have a higher performance service-rating in the field compared to the alternative products in the comparison test.

By incorporating a non permanent film on the outer surface of the splint material, the film supports the activated splint and restricts its deformation. The film also protects the users and allows the mesh to be cooled to ambient using water without wetting the underlying surface. On cooling the film can be removed. The splint packaging can be used as the functional film described above. In this case the packaging is used to tone polymer and a ligno-cellulose additive wherein the material is formable at a forming temperature above ambient temperature and is substantially rigid at ambient temperature and wherein the member has one or more openings through at least part thereof disposed such that the flexural strength of the member in a first direction is greater than that in a second direction.

2. The device as claimed in claim 1 wherein the material forming temperature is above 35° C.

3. The device as claimed in claim 2 wherein the material forming temperature is above 55° C.

4. The device as claimed in claim 1 wherein the polymer comprises a thermoplastic material.

5. The device as claimed in claim 1 wherein the polymer comprises a co-polymer.

6. The device as claimed in claim 1 wherein the additive material is provided in the form of a plurality of fibres.

7. The device as claimed in claim 1 wherein the fibres are dispersed throughout said polymer.

8. The device as claimed in claim 1 wherein at ambient temperature, the Young's modulus of the material is in the range of from 300 MPa to 2,500 MPa.

9. The device as claimed in claim 1 wherein the heat insulation properties of the material are such that it can be moulded by hand and applied on a person's limb.

10. The device as claimed in claim 9 wherein the material comprises at least 15% by weight ligno-cellulose.

11. The device as claimed in claim 9 wherein the material comprises at least 33% by weight ligno-cellulose.

12. The device as claimed in claim 1 wherein the additive material comprises wood.

13. The device is claimed in claim 1 wherein at the forming temperature the member is stretchable.

14. The device as claimed in claim 1 wherein the member comprises three or more substantially straight edges around at least one of the openings.

15. The device as claimed in claim 1 wherein one or more openings are substantially oval-shaped.

16. The device as claimed in claim 1 wherein the member comprises a mesh of elements.

17. The device as claimed in claim 16 wherein the mesh comprises a single uniform flat material, the mesh being movable relative to the openings due to a concertina effect and due to stretching of the member when the member is at the forming temperature.

18. The device as claimed in claim 16 wherein the combined effect of movement results in extensibility of up to plus 40% or minus 20% of the member.

19. The device as claimed in claim 16 wherein the width of at least one of the elements is in the range of from 2 mm to 12 mm.

20. The device as claimed in claim 16 wherein over at least part of the member, the percentage of the total cross-sectional area of the one or more openings to the total cross-sectional area of the member is in the range of from 1% to 80%.

21. The device as claimed in claim 1 where said first and second directions are substantially orthogonal with respect to each other.

22. The device as claimed in claim 21 wherein said first direction is a longitudinal direction.

23. The device as claimed in claim 21 wherein the second direction is a circumferential direction.

24. The device as claimed in claim 1 wherein the strength of the member in the second direction is in the range of from 10% to 95% of the strength of the member in the first direction.

25. The device as claimed in claim 1 wherein the member comprises a plurality of edges, rounded between the outer surface and each of the edges.

26. The device as claimed in claim 1, wherein the member has a three point bending strength to openness ratio ($S/O_u$) of the member being greater than 0.1, the $S/O_u$ being defined by:

$$S/O_u = F/V \times \% \ OA$$

wherein
F=Force (N) required, during a three-point bending test to deflect a sample of the member, having an area being tested of 100 cm$^2$, by 10 mm;
V=Volume (cm$^3$) of the sample of the member; and $$\% \ OA = \left\{ \frac{\text{The total area of the one or more openings}}{\text{The total area of the sample of the member}} \right\} \text{Expressed as a percentage,}$$

wherein the three-point bending test is conducted according to following steps:
placing the sample of 100 cm$^2$ horizontally and centrally on a centrally-hollowed lower support element;
vertically applying a central compression bending element onto the sample's central surface at a speed of 25 mm/min until 10 mm deflection is achieved, deflection being a horizontal distance traveled by an edge of the sample from a first position where the compression bending element does not contact the sample surface to a second position where the compression bending element contacts the sample surface.

27. The device as claimed in claim 26 wherein the $S/O_u$ is in the range of from 0.1 to 5.0.

28. The device as claimed in claim 1 wherein the member has a unidirectional bending strength to openness ratio ($S/O_u$) greater than 4, the $S/O_u$ being defined by:

$$S/O_u F/V \times \% \ OA$$

wherein
F=Force (N) required, during a unidirectional bending test to deflect a sample of the member, having an area being tested of 100 cm$^2$, by 10 mm;
V=Volume (cm$^3$) of the sample of the member; and $$\% \ OA = \left\{ \frac{\text{The total area of the one or more openings}}{\text{The total area of the sample of the member}} \right\} \text{Expressed as a percentage,}$$

wherein the unidirectional bending test is conducted according to following steps:
placing the sample of 100 cm$^2$ horizontally and centrally on a centrally-hollowed lower support element;
vertically applying a central compression bending element onto the sample's central surface at a speed of 25 mm/min until 10 mm deflection is achieved, deflection being a horizontal distance traveled by an edge of the sample from a first position where the compression bending element does not contact the sample surface to a second position where the compression bending element contacts the sample surface.

29. The device as claimed in claim 28 wherein the $S/O_u$ is in the range of from 4 to 20.

30. The device as claimed in claim 1 wherein the member comprises a first layer and a second layer, the second layer being configured to be located between the first layer of said member and an object being splinted and/or protected.

31. The device as claimed in claim 30 wherein the second layer is attached to the first layer.

32. The device according to claim 30 wherein the member or first layer of the composite member comprises a series of elements hinged together.

33. The device according to claim 30 wherein said member is a composite member, and the individual elements, defining the first layer are linked by the second layer.

34. A process for the manufacture of the protective and/or splint device according to claim 1 which comprises injection or compression moulding the composite material, the material being formable at a forming temperature above ambient temperature and substantially rigid at ambient temperature.

35. A protective and/or splint device comprising a protective and/or splint member, the member comprising one or more openings therethrough, over at least part of the member, and having a three point bending strength to openness ratio ($S/O_u$) of the member being greater than 0.1, the $S/O_u$ being defined by:

$$S/O_u = F/V \times \% OA$$

wherein
F=Force (N) required, during a unidirectional bending test to deflect a sample of the member, having an area being tested of 100 cm², by 10 mm;
V=Volume (cm³) of the sample of the member; and $$\% OA = \left\{ \frac{\text{The total area of the one or more openings}}{\text{The total area of the sample of the member}} \right\} \text{Expressed as a percentage,}$$

wherein the unidirectional bending test is conducted according to following steps:
placing the sample of 100 cm² horizontally and centrally on a centrally-hollowed lower support element;
vertically applying a central compression bending element onto the sample's central surface at a speed of 25 mm/min until 10 mm deflection is achieved, deflection being a horizontal distance traveled by an edge of the sample from a first position where the compression bending element does not contact the sample surface to a second position where the compression bending element contacts the sample surface.

36. A protective and/or splint device comprising a protective and/or splint member, the member comprising one or more openings there through, over at least part of the member, the unidirectional bending strength to openness ratio ($S/O_u$) of the member being greater than 4, the $S/O_u$ being defined by:

$$S/O_{11} = F/V \times \% OA$$

wherein
F=Force (N) required, during a unidirectional bending test to deflect a sample of the member, having an area being tested of 100 cm², by 10 mm;
V=Volume (cm³) of the sample of the member; and $$\% OA = \left\{ \frac{\text{The total area of the one or more openings}}{\text{The total area of the sample of the member}} \right\} \text{Expressed as a percentage,}$$

wherein the unidirectional bending test is conducted according to following steps:
placing the sample of 100 cm² horizontally and centrally on a centrally-hollowed lower support element;
vertically applying a central compression bending element onto the sample's central surface at a speed of 25 mm/min until 10 mm deflection is achieved, deflection being a horizontal distance traveled by an edge of the sample from a first position where the compression bending element does not contact the sample surface to a second position where the compression bending element contacts the sample surface.

* * * * *